(12) United States Patent
Cosgrove et al.

(10) Patent No.: US 10,392,423 B2
(45) Date of Patent: Aug. 27, 2019

(54) PEPTIDE-BASED INHIBITORS OF MLL/SET1 FAMILY CORE COMPLEXES

(71) Applicant: The Research Foundation for the State University of New York, Syracuse, NY (US)

(72) Inventors: Michael S. Cosgrove, Syracuse, NY (US); Nilda L. Alicea-Velazquez, Hamden, CT (US); Stephen A. Shinsky, Philadelphia, PA (US)

(73) Assignee: The Research Foundation for the State University of New York, Syracuse, NY (US)

( * ) Notice: Subject to any disclaimer, the term of this patent is extended or adjusted under 35 U.S.C. 154(b) by 0 days.

(21) Appl. No.: 15/939,604

(22) Filed: Mar. 29, 2018

(65) Prior Publication Data

US 2018/0282373 A1    Oct. 4, 2018

Related U.S. Application Data

(60) Provisional application No. 62/478,087, filed on Mar. 29, 2017.

(51) Int. Cl.
| | |
|---|---|
| *C07K 7/06* | (2006.01) |
| *A61K 45/06* | (2006.01) |
| *A61P 35/00* | (2006.01) |
| *A61K 38/08* | (2019.01) |
| *C07K 14/00* | (2006.01) |

(52) U.S. Cl.
CPC ............. *C07K 7/06* (2013.01); *A61K 38/08* (2013.01); *A61K 45/06* (2013.01); *A61P 35/00* (2018.01); *C07K 14/00* (2013.01)

(58) Field of Classification Search
CPC combination set(s) only.
See application file for complete search history.

(56) References Cited

U.S. PATENT DOCUMENTS 9,890,434 B2 *   2/2018  Wang ............ C12Y 114/11027
2004/0214272 A1 * 10/2004  La Rosa ............ C07H 21/04
                                                                    435/69.1

OTHER PUBLICATIONS

Alicea-Velazquez (Targeted Disruption of the Interaction between WD-40 Repeat Protein 5 (WDR5) and Mixed Lineage Leukemia (MLL)/SET1 Family Proteins Specifically Inhibits MLL1 and SETd1A Methyltransferase Complexes, JBC 2016, vol. 291:22357) (Year: 2016).*

* cited by examiner

*Primary Examiner* — Karlheinz R. Skowronek
*Assistant Examiner* — Khalid Kader
(74) *Attorney, Agent, or Firm* — Hodgson Russ LLP

(57) ABSTRACT

Provided are peptides, compositions comprising the peptides, and methods of using the peptide compositions for inhibition of growth of cancer cells. The peptides comprise a sequence of $ARX_1X_2X_3X_4$, and inhibit or disrupt the formation of MLL1 and SET1 complexes.

16 Claims, 8 Drawing Sheets

Specification includes a Sequence Listing.

PEPTIDE-BASED INHIBITORS OF MLL/SET1 FAMILY CORE COMPLEXES

CROSS REFERENCE TO RELATED APPLICATIONS

This application claims priority to U.S. Provisional Application No. 62/478,087, filed on Mar. 29, 2017, the disclosure of which is hereby incorporated by reference.

STATEMENT REGARDING FEDERALLY SPONSORED RESEARCH

This invention was made with government support under contract no. R01CA140522 awarded by the National Institutes of Health. The government has certain rights in the invention.

FIELD OF DISCLOSURE

This disclosure generally relates to compositions and methods for treatment of cancers and more particularly to treatment of cancer by disruption or inhibition of MLL1/SET1A complexes.

BACKGROUND OF THE DISCLOSURE

Mixed Lineage Leukemia 1 (MLL1) protein is a member of the SET1 family of histone methyltransferases. Others member of the human SET1 family include MLL2, MLL3, MLL4, SET1a and SET1b. Members of the SET1 family of proteins assemble into multisubunit complexes that regulate mono-, di- and trimethylation of proteins such as H3 histone protein (H3K4). Overproduction of the MLL1 core complex leads to excessive di- and trimethylation of H3K4 which disrupts gene regulation. This, in turn, alters hematopoiesis and normal development and has been linked to certain types of leukemia, solid tumors, and psychotropic disorders, such as schizophrenia and bipolar disorders.

It has been shown that the minimal complex required for di- and trimethylation of H3K4 includes MLL1, WDR5, RbBP5 and Ash2L, which together form the MLL1 core complex. The protein WDR5 has been shown to be critical for these interactions, as it bridges the catalytic SET domain of SET1 family proteins and the regulatory components of RbBP5 and Ash2L. Although the MLL1 core complex is a target of researchers, there are, as of yet, no approaches for inhibit the formation of SET1 family core complexes for the treatment of leukemia and other disorders.

SUMMARY OF THE DISCLOSURE

The present disclosure provides peptide-based inhibitors of SET1 family core complexes. These peptides can be used to inhibit the growth of cancer cells. These peptide inhibitors can inhibit the enzymatic activity of complexes of MLL1 and SETd1A. The peptide inhibitors may act via inhibiting the formation of or disrupt MLL1 and SETd1A complexes. The peptide inhibitors may also enhance the activity of MLL3, which is a known tumor suppressor.

In one aspect, this disclosure provides peptides comprising the sequence $ARX_1X_2X_3X_4$ (SEQ ID NO:1), where independently, $X_1$ can be A, S, L, V, W, Y, or T; $X_2$ can be E or Q; $X_3$ can be V, P, or G, and $X_4$ can be Y, K, or R. The peptides may be from 6 to 50 amino acids long. For example, the peptides can be 7, 10, 15, 20, 25, 30, 35, 40, 45, or 50 amino acids long, and all values therebetween. For example, the $ARX_1X_2X_3X_4$ (SEQ ID NO:1) sequence can be ARTEVY (SEQ ID NO:8) or ARTEPY (SEQ ID NO:9).

In one embodiment, the peptide of the present disclosure is 6 amino acids long and has the sequence $ARX_1X_2X_3X_4$ (SEQ ID NO:1), where independently, $X_1$ can be A, S, L, V, W, Y, or T; $X_2$ can be E or Q; $X_3$ can be V, P, or G, and $X_4$ can be Y, K, or R. Modifications to the terminal amino acids may be made. For example, the N-terminus of the peptide may be acetylated, and/or the C-terminus may be amidated. Other modifications may be made, such as, for example, to stabilize the peptide. As an example, intramolecular or intermolecular stapling can be carried out, which may stabilize the peptides.

In an aspect, this disclosure provides pharmaceutical compositions comprising one or more peptides of the present disclosure and a pharmaceutically acceptable carrier and/or excipients.

The peptides can be used for treating individuals with cancers associated with MLL1 and SETd1A. Examples of conditions that are associated with increased formation of MLL1 and SETd1A complexes include leukemia, such as infant acute lymphocytic leukemia and de novo acute myeloid leukemia, neuroblastoma, breast cancer, bladder cancer, pancreatic cancer, colorectal cancer, and other solid tumors with MLL1 overexpression, such as induced by P53 gain-of-function mutations.

In an aspect, this disclosure provides a method of inhibiting the growth of cancer cells comprising administering to an individual in need of treatment a composition of the present disclosure. The individual in need of treatment can be a human or a non-human animal, such as a domestic, farm or dairy animal. For example, the compositions may be administered to individuals whose condition is known to be associated with increased formation of MLL1 and SETd1A complexes, or overexpression of WDR5. The administration can be combined with chemotherapy, radiation therapy, surgical removal of tumors, or combinations thereof, and/or with a diagnostic technique.

DETAILED DESCRIPTION OF THE DISCLOSURE

Figure 1:
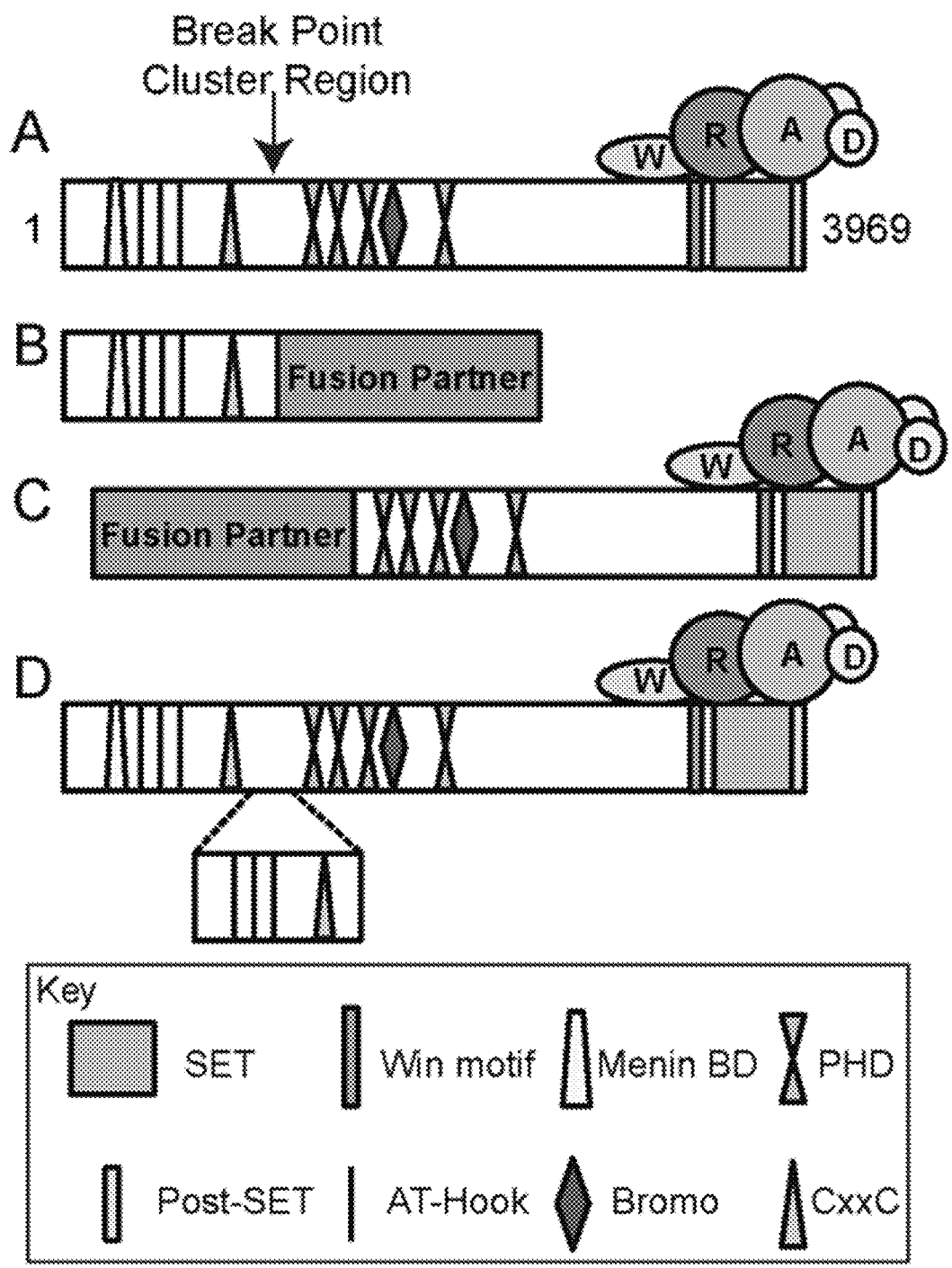
FIG. 1 shows a schematic of common outcomes of MLL1 genetic rearrangements. (A) Domain map of full-length wild type MLL1 with the breakpoint region denoted by an arrow. MLL1 contains many domains involved in binding chromatin (i.e. AT-Hooks, CxxC domains, PHD and Bromodomains) as well as domains involved in mediating protein-protein interactions (i.e. Menin binding domain (Menin BD) and the WDR5 Interaction (Win) motif). The SET and Post-SET domains are involved in catalysis. The WRAD sub-complex interacts with the C-terminus of MLL1. (B) Shows the most common outcome of MLL1 genetic rearrangements, which result in replacement of the C-terminus of MLL1 with one of ~70 known fusion partners (i.e. AF9, AF4, and ENL). In this arrangement the N-terminus is retained but the catalytic SET/Post-SET domain is lost. (C) Shows a rearrangement that results in the replacement of the N-terminus of MLL1 with a fusion partner (i.e. AF4). In this arrangement the N-terminal domains are lost, but the catalytic domain is retained. (D) Depicts a result of a partial tandem duplication in which a segment of the N-terminus (containing the AT-Hooks and CxxC domain) is duplicated and inserted at the break point region.

The human SET1 family is comprised of large proteins with several well-characterized functional domains involved in chromatin binding and protein-protein interactions (FIG. 1A). Most genetic rearrangements of MLL1 result in translocations that fuse the N-terminal fragment of the MLL1 protein (lacking the SET domain) to one of approximately 70 known fusion partners (FIG. 1B). Certain MLL1 gene rearrangements result in aberrant MLL1 proteins that retain the catalytic domain (FIG. 1C). Additionally, internal partial tandem duplications (FIG. 1D), which result in duplication of an N-terminal segment of MLL1 retaining the C-terminal SET domain, have been described in ~10% of AML patients and have been shown to play a dominant gain-of-function role in oncogenesis.

The present disclosure provides peptide-based inhibitors of MLL1 and SET1A complexes. The peptide-based inhibitors comprise the sequence ARX$_1$X$_2$X$_3$X$_4$ (SEQ ID NO:1).

The sequence $ARX_1X_2X_3X_4$ (SEQ ID NO:1) is referred to herein as Win6mer or as a 6-mer. The present disclosure also provides methods for treating cancers associated with MLL1 and SETd1A by inhibiting the formation of MLL1 and SETd1A complexes and/or inhibiting their enzyme activity.

As used herein, unless otherwise stated, the term "group," when used in the context of a chemical structure, refers to a chemical entity that has one terminus that can be covalently bonded to other chemical species. Examples of groups include, but are not limited to:

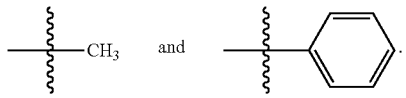

As used herein, unless otherwise stated, the term "moiety" refers to a chemical entity that has two or more termini that can be covalently bonded to other chemical species. Examples of moieties include, but are not limited to:

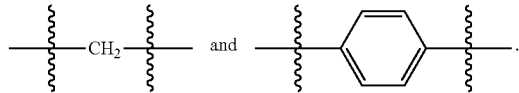

As used herein, unless otherwise indicated, the term "aliphatic" refers to branched or unbranched hydrocarbon groups that, optionally, contain one or more degrees of unsaturation (e.g., one or more pi bonds and cyclic groups/moieties). Aliphatic groups include, but are not limited to, alkyl groups/moieties, alkenyl groups/moieties, alkynyl groups/moieties, aryl groups/moieties, and cyclic aliphatic groups/moieties. For example, the aliphatic group/moiety can be a $C_1$ to $C_{30}$ aliphatic group/moiety, including all integer numbers of carbons and ranges of numbers of carbons therebetween. The aliphatic group can be unsubstituted or substituted with one or more substituents. Examples of substituents include, but are not limited to, halogens (—F, —Cl, —Br, and —I), additional aliphatic groups/moieties (e.g., alkanes, alkenes, alkynes, aryl groups/moieties), alkoxides, carboxylates, carboxylic acids, ether groups/moieties, hydroxyl groups, and the like, and combinations thereof.

The peptides of the present disclosure comprise the following sequence: $ARX_1X_2X_3X_4$ (SEQ ID NO:1), where $X_1$ can be A, S, L, V, W, Y, or T; $X_2$ can be E or Q; $X_3$ can be V, P, or G; and $X_4$ can be Y, K, or R. The peptides can have any combination of the listed amino acids. The peptides can be acetylated at the N-terminus and/or amidated at the C-terminus, or otherwise modified to increase stability, cell membrane permeability, improved biological properties, increased affinity for target, or effectiveness in any other way.

The peptides can include naturally-occurring amino acids, amino acid analogs (also referred to herein as amino acid mimics), and synthetic amino acids (also referred to herein as non-natural amino acids). The term "amino acid" refers to a molecule containing both an amino group and a carboxyl group bound to a carbon which is designated the α-carbon. Suitable amino acids include, without limitation, the D- and L-isomers of naturally-occurring amino acids, non-naturally occurring amino acids. and amino acid analogs. The amino acids may be prepared by organic synthesis or other metabolic routes. The term "naturally occurring" or "natural" amino acids refers to any one of the twenty amino acids found in proteins synthesized in nature, and known by the one letter abbreviations A (alanine), R (arginine), N (asparagine), C (cysteine), D (aspartic acid), Q (glutamine), E (glutamic acid), G (glycine), H (histidine), I (isoleucine), L (leucine), K (lysine), M (methionine), F (phenylalanine), P (proline), S (serine), T (threonine), W (tryptophan), Y (tyrosine) and V (valine). The term "amino acid analog" refers to an amino acid-like molecule, which is a molecule having a first terminus having a nucleophile (e.g., an amine group, alcohol group, thiol group, and the like); a second terminus having an electrophile (e.g., carboxylic acid group, an acyl chloride group, an ester group, and the like); at least one atom (e.g., a carbon atom) between the termini; and a side chain (e.g., H, an aliphatic group, and the like). Such a side chain can be attached (e.g., covalently bonded) to any one of the at least one atoms between the termini, or to one or both of the termini (e.g., an N-substituted glycine). Examples of specific classes of amino acid analogs include, but are not limited to, functionalized 2-hydroxyacetic acids (e.g., a 2-hydroxyacetic acid functionalized at the α-carbon, such as, for example, 2-hydroxypropanoic acid, 2-hydroxy-3-phenylpropanoic acid, and the like), N-substituted glycines (e.g., N-substituted glycines where nitrogen is substituted with, for example, an aliphatic group or the like), and aliphatic linkers (e.g., β-alanine, 6-aminohexanoic acid, 6-hydroxyhexanoic acid, and the like). The term "synthetic amino acid" includes ornithine and selenocysteine and non-proteinogenic amino acids (additional examples of non-natural amino acids can be found in Liu & Schultz, Adding New Chemistries to the Genetic Code, Annu. Rev. Biochem. 2010, 79, 413-44, the relevant portions of which are hereby incorporated by reference). The terms "peptide," "peptide inhibitors," or "peptide based inhibitors" as used in this disclosure means the molecules disclosed with the understanding that the molecules can include natural amino acids, non-natural amino acids, and amino acid analogs.

In an embodiment, the peptide is 6 amino acid residues long and has the sequence $ARX_1X_2X_3X_4$ (SEQ ID NO:1), where $X_1$ can be A, S, L, V, W, Y, or T; $X_2$ can be E or Q; $X_3$ can be V, P, or G; and $X_4$ can be Y, K, or R. The peptide can have any combination of the listed amino acids. The peptides can be acetylated at the N-terminus and/or amidated at the C-terminus.

In another embodiment, the peptide has a sequence comprising the following sequence: $ARX_1X_2X_3X_4$ (SEQ ID NO:1), where $X_1$ can be A, S, L, V, W, Y, or T; $X_2$ can be E or Q; $X_3$ can be V, P, or G; and $X_4$ can be Y, K, or R, where the peptide has a total of 7-50 amino acid residues, including all amino acid residue lengths and ranges therebetween. The peptide can comprise natural amino acid residues, non-natural amino acid residues, and amino acid analog residues. The peptides can be acetylated at the N-terminus and/or amidated at the C-terminus.

The peptides of the disclosure may adopt secondary structures. For example, the peptides can adopt an alpha helical formation. The formed helix can be a $3_{10}$ alpha helix. The peptides are peptidomimetics of the Win-motif of MLL. The peptides can bind to WDR5 in a $3_{10}$ helical conformation. When the N-terminus is acetylated, it can provide a hydrogen bond acceptor that may help stabilize the $3_{10}$ helix.

While not intending to be bound by any particular theory, it is considered that $X_2$ may form a hydrogen bond with the acetyl moiety on the N-terminus and stabilizes the $3_{10}$ helix, $X_3$ may provide proper positioning of the $X_4$ residue, and $X_4$ may provide high affinity binding by forming a hydrogen bond with the conserved aspartate 172 from WDR5.

The peptides can be synthesized through methods known in the art (e.g., recombinant expression or solid phase peptide synthesis (SPPS)).

In specific embodiments, the 6-mer peptide can have the sequence ARTEVY (SEQ ID NO:8), or ARTEPY (SEQ ID NO:9). The peptides may be acetylated at the N-terminus and amidated at the C-terminus and therefore can be represented as: Ac-ARTEVY-NH$_2$ (SEQ ID NO:8, where the N-terminus is acetylated and the C-terminus is amidated) or Ac-ARTEPY-NH$_2$ (SEQ ID NO:9, where the N-terminus is acetylated and the C-terminus is amidated).

The peptides of the present disclosure may be conjugated to cell penetrating peptides (CPPs). The peptides can be conjugated to the N-terminus or the C-terminus of the CPPs. For example, a HIV-TAT peptide may be used. An example of a HIV-TAT cell penetrating sequence is YGRKKRRQRRR (SEQ ID NO:10). For example, ARX$_1$X$_2$X$_3$X$_4$ (SEQ ID NO:1), or a peptide comprising the sequence of SEQ ID NO:1, where X$_1$ is A, S, L, V, W, Y, or T; X$_2$ is E or Q; X$_3$ is V, P, or G; and X$_4$ is Y, K, or R, can be conjugated to the N-terminus or C-terminus of YGRKKRRQRRR (SEQ ID NO:10).

The peptides of the present disclosure may be stabilized by techniques known in the art (e.g., stapling, α-methylation, N-capping, and side-chain-to-side-chain cross-linking). The term "stapling" as used herein refers to the intramolecular or intermolecular connection (also referred to as cross-linking) of two peptides or two peptide domains (e.g., two loops of a helical peptide). An intermolecular connection can be several connections (e.g., at least one connection is required to link two peptides) linking (e.g., covalently bonding) an additional 1, 2, 3, or more peptides together. A stapled peptide with intramolecular staple(s) comprises at least one pair of functionalized amino acids, wherein the functionalized amino acids are joined by a staple. A staple can be any cross-linking moiety. The amino acids involved may be natural amino acids, non-natural amino acids, or amino acid analogs. Stapling techniques are known in the art. For example, a summary of the design and properties of stapled peptides can be found in Hydrocarbon Stapled Peptides as Modulators of Biological Function, Cromm et al. ACS Chemical Biology 2015 10 (6), 1362-75, the relevant portions of which are incorporated by reference herein.

When the peptide has a helical secondary structure, the staple can be an aliphatic linking moiety, which is not part of the core or inherent (non-stapled) helical peptide structure. The aliphatic linking moiety incorporates (e.g., covalently bonds to) at least two amino acids of the peptide. In various embodiments, the stapled peptide has 1, 2, or 3 staples. Aliphatic linking moieties used for stapling can be of a size and/or rigidity that provide desirable stabilization of a helical motif of a peptide or a helical segment of a peptide. The distance matching and/or rigidity of the aliphatic linking moiety may be such that the stapled peptide has increased helicity relative to proteins and peptides that are not cross linked. Stapling can also occur between two cysteine, α-alkylcysteine (e.g., α-methylcysteine residues), other suitable amino acids (e.g., serine, lysine, and/or non-natural amino acids), or combinations thereof (e.g., stapling can occur between two different amino acid). U.S. Pat. No. 8,586,707 provides examples of stapling of peptides (incorporated herein by reference).

The amino acid residues involved in the staple connection are designated to be at the i and i+n positions of a peptide, where n could be 1-49, including all amino acid values and ranges therebetween, for a 50-mer peptide. "i" denotes a first natural or non-natural amino acid residue involved in the staple and i+n denotes a second natural or non-natural amino acid residue involved in the staple. The staple can involve any amino acid in the peptide. In one embodiment, in α-helical configurations, the stapled amino acids may be i, i+3; i, i+7; i, i+10 and so on.

The peptides of the present disclosure inhibit formation of MLL1 and SETd1A complexes. In one embodiment, the peptides may not inhibit the enzymatic activity of complexes of MLL2, MLL3, MLL4, or SETd1B. The peptide inhibitors have a strong affinity (K$_d$) for WDR5. The affinity may be in the nanomolar range. For example, the K$_d$ can be 2 to 3000 nM, including all integer nM values and ranges therebetween.

In one aspect, the disclosure provides compositions, including pharmaceutical compositions comprising the present peptides. The pharmaceutical compositions may comprise one or more peptides and an acceptable pharmaceutical carrier or excipient. The carriers or excipient are "acceptable" in the sense of being compatible with the other ingredients of the formulation and not deleterious to the recipient thereof. Examples of pharmaceutically-acceptable carriers or excipients include pharmaceutically-acceptable material, composition or vehicle, such as a liquid or solid filler, diluents, bulking agents, stabilizers, solvent or encapsulating material involved in carrying or transporting the subject chemical from one organ, or portion of the body, to another organ, or portion of the body, or stabilizing the active ingredient. Examples of pharmaceutically acceptable carriers, excipients, and stabilizers can be found in *Remington: The Science and Practice of Pharmacy* (2005) 21st Edition, Philadelphia, Pa. Lippincott Williams & Wilkins. For example, suitable carriers or excipients which are non-toxic to recipients at the dosages and concentrations employed, can include buffers such as, for example, acetate, Tris, phosphate, citrate, and other organic acids; antioxidants including ascorbic acid and methionine; preservatives such as, for example, octadecyldimethylbenzyl ammonium chloride; hexamethonium chloride; benzalkonium chloride, benzethonium chloride; phenol, butyl or benzyl alcohol; alkyl parabens such as, for example, methyl or propyl paraben; catechol; resorcinol; cyclohexanol; 3-pentanol; and m-cresol; amino acids such as, for example, glycine, glutamine, asparagine, histidine, arginine, or lysine; monosaccharides, disaccharides, and other carbohydrates including glucose, mannose, or dextrins; chelating agents such as, for example, EDTA; tonicifiers such as, for example, trehalose and sodium chloride; sugars such as, for example, sucrose, mannitol, trehalose or sorbitol; surfactant such as, for example, polysorbate; salt-forming counter-ions such as, for example, sodium; and/or non-ionic surfactants such as, for example, Tween or polyethylene glycol (PEG). The pharmaceutical compositions may comprise other therapeutic agents. The present compositions can be provided as single doses or in multiple doses covering the entire or partial treatment regimen. The compositions can be provided in liquid, solid, semi-solid, gel, aerosolized, vaporized, or any other form from which it can be delivered to an individual.

In one embodiment, the peptides of the present disclosure may be the only active peptides in the composition that can inhibit formation of MLL1 and SETd1A complexes. In one embodiment, the peptides of the present disclosure are the only peptides or proteins present in the composition.

In an aspect, the present disclosure provides a method of using the peptide inhibitors. For example, the peptide-based inhibitors can be used for inhibiting formation of complexes of MLL1 and SETd1A or disrupt already formed complexes of MLL1 and SETd1A. As such, the present peptide inhibitors can be used for treatment of cancers associated with MLL1, SETd1A or WDR5 overexpression. For example, the present peptides can be used for treatment of leukemia; such as, for example, infant acute lymphocytic leukemia and de novo acute myeloid leukemia. Additional examples of cancers include, but are not limited to, neuroblastoma, breast cancer, bladder cancer, pancreatic cancer, colorectal cancer, and other solid tumors.

Pharmaceutical compositions comprising, consisting essentially of, or consisting of the present peptides can be administered to an individual in need of treatment for inhibiting formation of MLL1 and SETd1A complexes and/or treating an individual having one or more cancers. The individual in need of treatment can be a human or a non-human animal, such as a domestic, farm or dairy animal. Clinicians will be able to assess individuals who are in need of being treated for these conditions. The present compositions can be used in combination with other diagnostic approaches and/or therapeutic approaches for the conditions. For example, the present compositions may be used in conjunction with chemotherapy, radiation therapy, surgical removal of tumors and any other type of therapy. The additional therapeutic approaches can be carried out sequentially or simultaneously with the treatment involving the present compositions. As used herein, "treatment" of a condition (such as cancer) is not limited to complete cure, but encompasses alleviation of the symptoms associated with that condition.

Administration of formulations comprising peptide inhibitors as described herein can be carried out using any suitable route of administration known in the art. For example, the compositions may be administered via intravenous, intramuscular, intraperitoneal, intracerobrospinal, subcutaneous, intra-articular, intrasynovial, oral, topical, or inhalation routes. The compositions may be administered parenterally or enterically. The compositions may be introduced as a single administration or as multiple administrations or may be introduced in a continuous manner over a period of time. For example, the administration(s) can be a pre-specified number of administrations or daily, weekly or monthly administrations, which may be continuous or intermittent, as may be clinically needed and/or therapeutically indicated. The compositions may be administered to an individual in need of treatment such as a human, or a non-human animal.

The steps of the methods described in the various embodiments and examples disclosed herein are sufficient to carry out the methods of the present invention. Thus, in an embodiment, a method consists essentially of a combination of the steps of the methods disclosed herein. In another embodiment, a method consists of such steps.

The following examples are presented to illustrate the present disclosure. They are not intended to be limiting in any matter.

Example 1

This example provides a description of characterization of the Win motif in the core complex assembly and enzymatic activity for each human SET1 family complex.

MLL1 belongs to the SET1 family of histone H3 lysine 4 (H3K4) methyltransferases, comprised of MLL1-4 and SETd1A/B. MLL1 translocations are present in acute leukemias and mutations in several family members are associated with cancer and developmental disorders. MLL1 associates with a sub-complex containing WDR5, RbBP5, ASH2L, and DPY-30 (WRAD), forming the MLL1 core complex required for H3K4 mono- and dimethylation and transcriptional activation. Core complex assembly requires interaction of WDR5 with the MLL1 WDR5 interaction (Win) motif, which is conserved across the SET1 family. Agents that mimic the SET1 family Win motif inhibit the MLL1 core complex and have become an attractive approach for targeting MLL1 in cancers. Like MLL1 other SET1 family members interact with WRAD, but the roles of the Win motif in complex assembly and enzymatic activity remain unexplored. Here, we disclose that the Win motif is necessary for interaction of WDR5 with all members of the human SET1 family. Mutation of the Win motif-WDR5 interface severely disrupts assembly and activity of MLL1 and SETd1A complexes, but only modestly disrupts MLL2/4 and SETd1B complexes without significantly altering enzymatic activity in vitro. Notably, in the absence of WDR5, MLL3 interacts with RAD and shows enhanced activity. To further probe the role of the Win motif-WDR5 interaction, we designed a peptidomimetic that binds WDR5 (Kd~3 nM) and selectively inhibits activity of MLL1 and SETd1A core complexes within the SET1 family. Our results reveal that SET1 family complexes with the weakest Win motif-WDR5 interaction are more susceptible to Win motif-based inhibitors.

In this example, we disclose that all SET1 family members interact with WDR5 in a Win motif-dependent manner, but not all complexes are affected by disruption of the interaction in a similar way. Loss of WDR5-Win motif interaction severely destabilizes MLL1 and SETd1A complexes, moderately destabilizes MLL2-4 complexes, but does not affect the stability of the MLL3 core complex. To further probe the role of the WDR5-Win motif interaction among family members, we designed a 6-residue Win-motif peptidomimetic (Win6mer) that binds to WDR5 with high affinity ($K_d$~3 nM) and found that it inhibits MLL1 and SETd1A complexes, but does not inhibit MLL2-4 or SETd1B complexes. This disclosure reveals that the contributions of the Win motif-WDR5 interaction to complex assembly differ among the human SET1 family members and that such differences can be exploited to alter the enzymatic activities of a subset of SET1 family core complexes. In addition, our results reveal that the MLL1 and SETd1A complexes that bind WDR5 with the weakest affinity are most sensitive to inhibition by molecules that mimic the Win motif.

Figure 2:
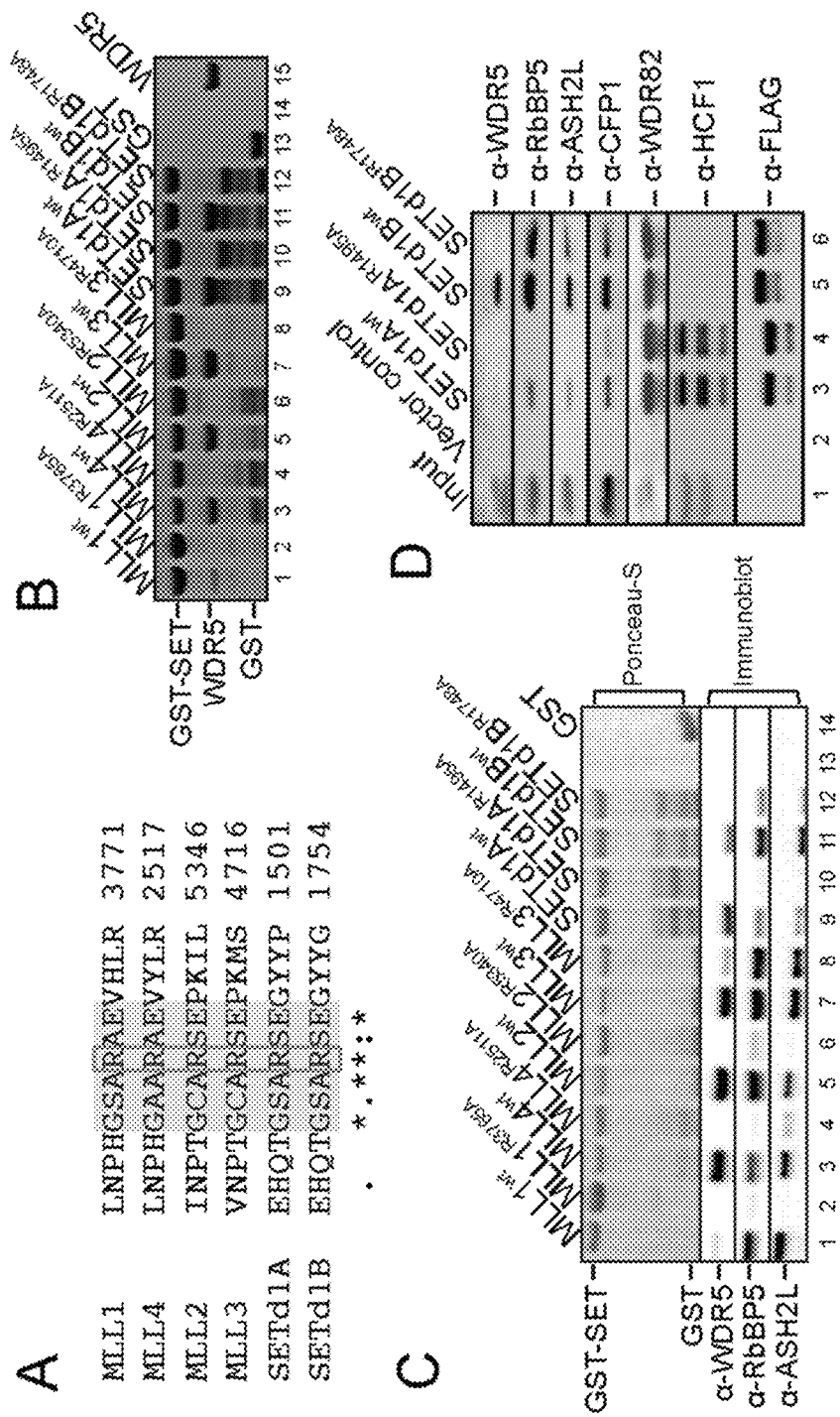
FIG. 2 shows the Win motif is required for interaction with WDR5. (A) Sequence alignment of the human SET1 family Win motif generated using Clustal Omega. The 6-residue Win motif is highlighted in grey and the conserved arginine is enclosed in a box. MLL1 is SEQ ID NO:2, MLL4 is SEQ ID NO:3, MLL2 is SEQ ID NO:4, MLL3 is SEQ ID NO:5, SETd1A is SEQ ID NO:6, and, SETd1B is SEQ ID NO:7. (B) GST-pull down of wild type and Win mutant SET1 family members with WDR5. Individual GST-tagged SET domains (wild type or mutant) were incubated with purified WDR5 and glutathione-coated agarose beads. Coomassie Blue stained SDS-PAGE gel of the pull-down fractions only is shown. GST was used as a negative control (lane 13), and a sample of purified WDR5 was run on the gel to compare the migration of pull-down bands (lane 15). (C) Comparison of wild type or mutant GST-SET domain pull-downs of WDR5, RbBP5, and ASH2L from MCF-7 cell extracts. WRA components were detected by Western blotting. The upper panel shows a Ponceau S-stained PVDF membrane and the lower panels show the immunoblots. (D) Comparison of wild type or Win motif mutant Flag tagged full-length SETd1A and SETd1B co-immunoprecipitation with WDR5, RbBP5, ASH2L, CFP1, WDR82, and HCF1 from stably transfected T-REx HEK293 cells.

Characterization of the contributions of the Win motif to complex assembly: The Win motif is a highly conserved region within the SET1 family and is comprised of 6 key residues located N-terminal to the catalytic domain (FIG. 2A). This region was previously identified as necessary for the pairwise interaction of MLL1 with WDR5 and for the assembly of the MLL1 core complex. However, unlike MLL1, MLL3 does not require interaction with WDR5 to stably interact with RbBP5/ASH2L. Furthermore, a recent study suggested that SET1 family members, with the exception of MLL1, do not require WDR5 to assemble a fully functional core complex. These results raise questions about the role of the Win motif and why it is so highly conserved among metazoan SET1 family enzymes. Thus, we set out to further characterize the roles of the Win motif in SET1 family core complex assembly.

To determine if the Win motif is required for direct interaction with WDR5, we first mutated the Win motif arginine to alanine in each SET1 family member and purified each recombinant protein as a GST-fusion. We then compared the ability of wild type and mutant SET1 family members to interact with WDR5 using a GST pull-down assay (FIG. 2B). We observed that all SET1 family members pulled down recombinant WDR5 (lanes 1, 3, 5, 7, 9, and 11), while the control GST protein lacking a SET1 family member did not (lane 13). Consistent with having the weakest Win motif-WDR5 interaction, MLL1 pulled down the least amount of WDR5. In contrast, all SET1 family members containing a mutated Win motif did not pull down WDR5 (lanes 2, 4, 6, 8, 10, and 12). These results suggest that all SET1 family members directly interact with WDR5 in a Win motif-dependent manner.

We then investigated the impact of disruption of Win motif-WDR5 interaction on SET1 family core complex stability. We compared the ability of wild type and Win motif mutant SET1 family GST-proteins to pull down endogenous WRAD components from MCF-7 breast cancer cell extracts using GST pull-down assays (FIG. 2C). While all wild-type SET1 family GST-proteins were able to interact with endogenous WRAD components (lanes 1, 3, 5, 7, 9, and 11), we noticed that mutant SET1 family members differed in their ability to interact with WRAD (lanes 2, 4, 6, 8, 10, and 12). Substitution of each Win motif arginine with alanine resulted in disruption of the SET domain-WDR5 interaction in all complexes, consistent with the Win motif playing a role in direct interaction with WDR5. In addition, all complexes, with the exception of the MLL3 core complex, showed reduced interactions with RbBP5 and ASH2L, but to varying degrees. Substitution of the Win motif arginine in the MLL1 and SETd1A constructs nearly abolished core complex assembly, whereas MLL2 and MLL4 showed weak interactions with RbBP5 and ASH2L, respectively. Substitution of the Win motif arginine in SETd1B$^{R1748A}$ pulled down RbBP5 and ASH2L, but to a lesser degree compared to wild type SETd1B (FIG. 2C, lanes 11 and 12). While MLL3$^{R4710A}$ showed a decreased interaction with WDR5, its ability to interact with RbBP5/ASH2L components was similar to that of wild type MLL3 (FIG. 2C, lanes 7 and 8), consistent with previous findings. These results demonstrate the importance of the Win motif for the interaction of WDR5 with each SET1 family core complex, but also reveal differences in the role WDR5 plays in complex stability in vitro.

To determine if the same differences are observed in cells, we selected the closely related SETd1A and SETd1B family members to further probe the role of the WDR5-Win motif interaction in mammalian cells. We stably transfected HEK293 cells with full-length human SETd1A and SETd1B constructs and compared the ability of wild type and Win motif mutant variants to co-immunoprecipitate endogenous WRAD components. Similar to the results of the GST pull-down assays, we found that substitution of the Win motif arginine with alanine abolished the interaction with WDR5 in both complexes (FIG. 2D, compare lanes 3 and 4; 5 and 6, respectively). In addition, loss of the WDR5-Win motif interaction severely disrupts SETd1A interaction with RbBP5 and ASH2L, whereas the same interactions were only modestly reduced when the SETd1B Win motif arginine was replaced with alanine. Despite these changes, substitution of the Win motif arginine with alanine did not significantly affect the ability of either protein to co-immunoprecipitate with SETd1A/B interacting proteins CFP1, WDR82, and HCF1. These data confirm the results obtained from the GST pull-down experiments and suggest that amino acid variation between SETd1A and SETd1B proteins account for the ability of RbBP5/ASH2L to interact with the SET domain in the absence of WDR5.

Altogether, these results demonstrate that all SET1 family members require the Win motif for interaction with WDR5. Moreover, while the Win motif-WDR5 interaction is not required for the interaction between MLL3 and RbBP5/ASH2L, it is required for the stability of the MLL1, MLL2, MLL4, SETd1A, and SETd1B core complexes, but to different degrees.

Contributions of the Win motif to SET1 family histone methyltransferase activity. We previously reported that substitution of the MLL1 Win motif arginine with alanine reduces core complex H3K4 dimethylation activity while a similar substitution in the MLL3 Win motif increases core complex H3K4 monomethylation activity. The contributions of the Win motif to the methyltransferase activity of the other SET1 family core complexes remain to be explored.

To address this knowledge gap, we compared the enzymatic activity of core complexes assembled with wild type or with Win motif mutant SET1 family proteins using histone H3 peptides (residues 1-20) that were unmodified (H3K4me0), mono- (H3K4me1), or dimethylated (H3K4me2) at lysine 4 as substrates. Reaction mixtures were separated by SDS-PAGE and imaged by fluorography (FIG. 3A). Quantitative measurements were obtained by excising peptide bands from the gels for liquid scintillation counting (FIG. 3B) as described in Experimental Procedures. The results upon mutation of each Win motif are highly similar to our previously reported assays with wild type complexes in absence of WDR5. When each complex was incubated with $^3$H-methyl-S-adenosylmethionine ($^3$H-AdoMet) and the H3K4me0 peptide, we observed that methylation levels were similar between wild type and Win motif variants, with the exception of the mutant MLL3 core complex, which showed approximately 2-fold more activity than the wild-type MLL3 core complex (FIG. 3A lanes 4 and 11 & FIG. 3B upper panel). These results indicate that despite the substitution of each Win motif arginine with alanine, the proteins are still folded and enzymatically active.

Figure 3:
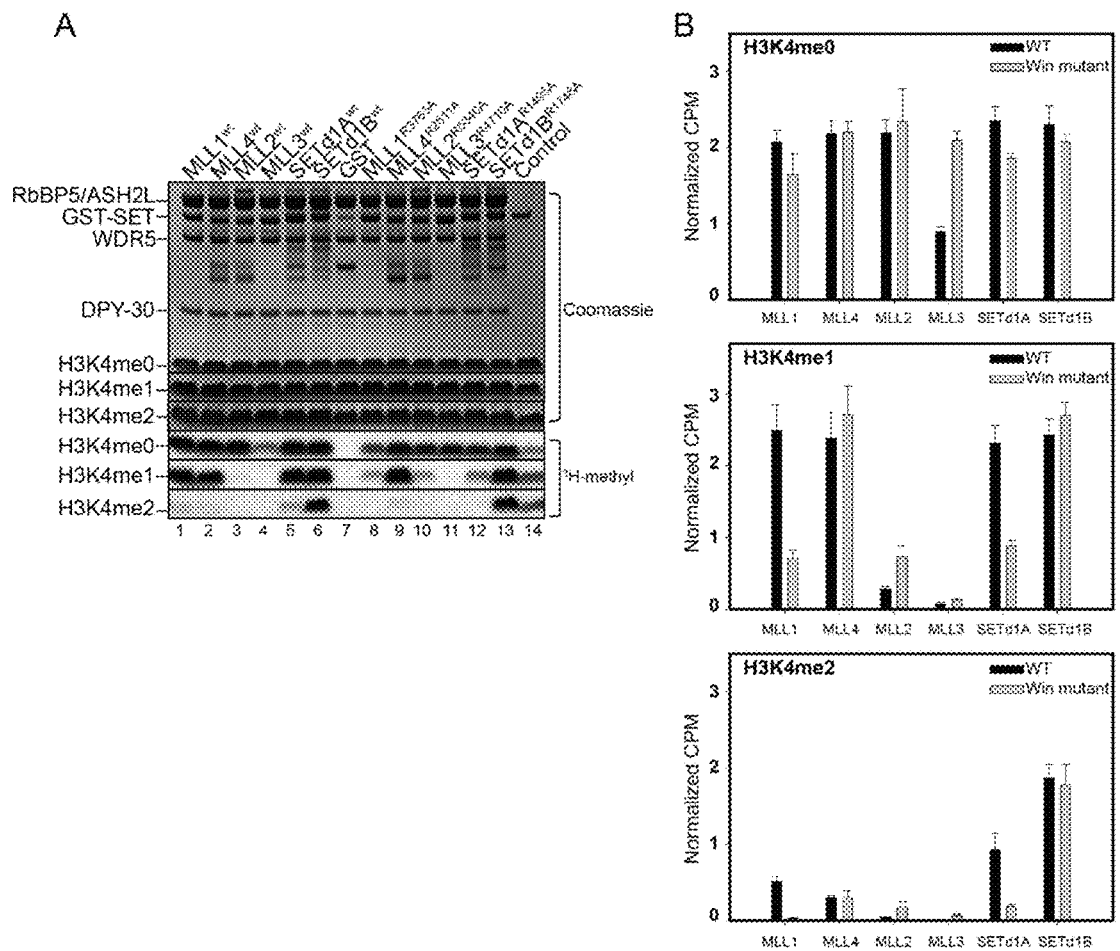
FIG. 3 shows a substitution of the Win motif arginine alters SET1 core complex-catalyzed H3K4 methyltransferase activity in vitro. (A) Sample gel showing the comparison of core complex methyltransferase activities among SET1 family members (wild type and mutant) in the presence of WRAD. The upper panels shows Coomassie Blue stained SDS-PAGE gels and the lower panels show $^3$H-methyl incorporation after 4 h of exposure as detected by fluorography. The control lane shows the activity of the MLL1$^{wt}$ SET domain with 100 µM H3K4me0 peptide, which is included on each gel. (B) Quantification of radioactivity from excised histone H3 bands by liquid scintillation counting (LSC). Data are normalized to the activity level of the control lane on each gel. Error bars represent the S. E. of measurement among three independent experiments.

In contrast, when H3K4me1 and H3K4me2 peptides were used as substrates, MLL1 and SETd1A complexes showed significant differences in activity between wild type and Win motif variants. Complexes assembled with MLL1 and SETd1A Win motif variants showed at least a 2-fold reduction in activity compared to their wild-type counterparts (FIG. 3A, compare lanes 1 and 8, and 5 and 12 & FIG. 3B middle and lower panels). Conversely, complexes assembled with MLL4 and SETd1B Win motif variants showed similar amounts of activity compared to that of their wild-type counterparts (FIG. 3A, compare lanes 2 and 9, and 6 and 13 & FIG. 3B middle panel). Interestingly, while the wild type MLL2 core complex catalyzes trace amounts of H3K4 dimethylation above background in vitro (FIG. 3 lane 3, and FIG. 3B), we observed a 2-fold increase in this activity with the MLL2 Win motif variant (FIG. 3, lane 10, and FIG. 3B). These results are similar to the stimulation of the monomethylation activity of MLL3 and MLL2 core complexes in the absence of WDR5. In contrast, both wild type and Win motif mutant MLL3 core complexes showed negligible activity with H3K4me1/2 substrates.

Together, these results demonstrate that the Win motif is required for the full methyltransferase activity of MLL1 and SETd1A complexes, consistent with the central role of WDR5 in their assembly. In contrast, despite the moderate destabilization of MLL2, MLL4 and SETd1B core complexes upon mutation of the Win motif, the complexes retain a sufficient amount of interaction with the RbBP5/ASH2L heterodimer to allow near full enzymatic activity in the absence of the Win-motif WDR5 interaction under these conditions. These results suggest that targeting the WDR5-Win motif interaction may be a useful strategy for selective inhibition of the MLL1 and SETd1A complexes.

Structure-based design and characterization of a new high affinity Win motif peptidomimetic. Our data suggest that SET1 family core complex stability and enzymatic activity are regulated by Win motif-WDR5 interaction to different extents. To test if molecules designed to disrupt this interface mainly affect MLL1 and SETd1A core complexes as they more strongly rely on WDR5 for assembly and function, we designed and characterized a new Win motif peptidomimetic and tested its inhibition properties against all six human SET1 family core complexes. We have shown that 14-residue peptides derived from the naturally occurring Win motif sequences of SET1 family members inhibit the dimethylation activity of the MLL1 core complex. Structure-function analyses showed that each peptide binds to WDR5 in a similar manner, but with a wide range of affinities (50-2800 nM) (Table I). In some peptides with the highest affinity for WDR5, we found an additional hydrogen bond between the fourth residue C-terminal to the Win motif arginine and the conserved Asp172 in WDR5 that was absent in complexes with lower affinities. In addition, we found that valine in the P+3 position (three residues C-terminal to the crucial arginine residue, denoted as P0) is expected to promote a conformation that places a tyrosine at the P+4 position in an optimal orientation to form this hydrogen bond. In the present disclosure, we synthesized a six-residue peptidomimetic. This peptide combined the best features of high affinity binding peptides while minimizing its overall size. The sequence contained amino acid residues ARTEVY (SEQ ID NO:8) and was acetylated on the N-terminus and amidated on the C-terminus to promote stability (Ac-ARTEVY-NH$_2$, (SEQ ID NO:8, where the N-terminus is acetylated and the C-terminus is amidated)). Thermodynamic binding measurements using isothermal titration calorimetry (ITC) revealed that ARTEVY (SEQ ID NO:8) binds to WDR5 with a K$_d$ of 2.9 nM (1.7-4.2 nM, 95% confidence interval) (FIG. 4A), which is an ~18-fold increase in binding affinity over the best naturally occurring Win motif sequence (Table I).

TABLE I

Binding affinities of Win motif-based MLL1 inhibitors towards WDR5 as determined by Isothermal Titration Calorimetry.

| Win motif mimetic | Dissociation Constant K$_d$ ± S.D. (nM) | |
| --- | --- | --- |
| MLL1* | 2762 | ±338 |
| MLL4* | 88 | ±6 |
| MLL2* | 75 | ±5 |
| MLL3* | 54 | ±5 |
| SETd1A* | 541 | ±46 |
| SETd1B* | 103 | ±14 |
| Win6mer | 2.9 | [1.7-4.2]† |
| WDR5-0103 | 450 | ±0.02 |
| OICR-9429 | 93 | ±28 |

*Indicates peptides derived from the native Win motif sequence of each SET1 family member.
†Indicates 95% confidence interval of determined dissociation constant.

Figure 4:
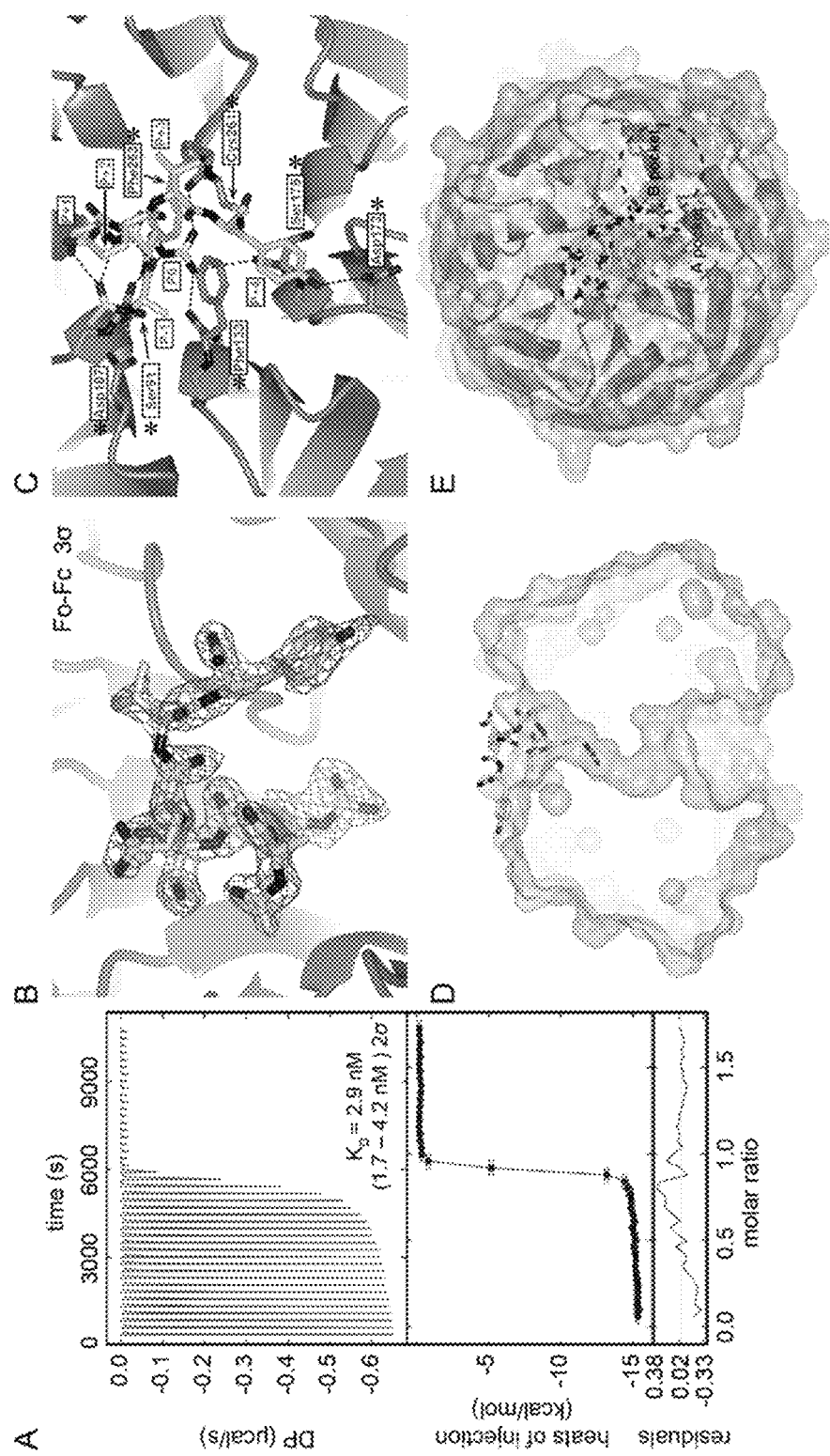
FIG. 4 shows a co-crystal structure of Win6mer and WDR5 at 2.0 Å resolution. (A) Thermodynamic characterization of the WDR5/Win6mer interaction by ITC. The binding affinity $K_d$ is reported with a confidence interval of 2σ or 95%. (B) Simulated annealing Fo-Fc omit map contoured at 3σ unambiguously shows electron density corresponding to the Win6mer peptide. (C) Intra-Win6mer and Win6mer-WDR5 bonding network. Hydrogen bonds are represented by dashed lines. Participating residues are labeled for Win6mer and labeled and marked with an asterisk for WDR5. Position "P0" corresponds to the conserved arginine residue. Positions P− and P+ correspond to residues N- and C-terminal from P0, respectively. (D) Cutaway of a surface rendition of the Win6mer/WDR5 structure. The conserved arginine is inserted into the Win motif binding pocket in WDR5. (E) Overlay of the MLL1 Win motif peptide (PDB ID 3EG6) and Win6mer peptide. The conserved arginines are oriented in a highly similar manner within the central cavity in WDR5. The P+4 residue in both peptides binds the A-pocket and not the B-pocket.

To determine if ARTEVY (SEQ ID NO:8) binds WDR5 in a similar manner to other Win motif peptides, we determined the co-crystal structure of the ARTEVY (SEQ ID NO:8)-WDR5 complex at 2.0 Å resolution (FIG. 4B-E). Data collection and refinement statistics are summarized in Table II. The overall structure of WDR5 was highly similar to previously reported structures, consisting of a seven-blade β-propeller with a cavity through the center of the protein (FIGS. 4D and E). This central cavity is denoted as the "Win motif-binding pocket" as previous co-crystal structures of WDR5 with SET1 family Win motif peptides have shown it to be the binding site of the conserved Win motif arginine. A simulated annealing Fo-Fc omit map contoured at 3σ unambiguously shows density for the peptide in the co-crystal structure in the Win motif-binding pocket (FIG. 4B), indicating that it does indeed bind in a similar manner to that of other Win motif peptides.

ARTEVY (SEQ ID NO:8) binds to WDR5 in a 3$_{10}$-helical conformation with the conserved arginine (P0) inserted into the Win motif-binding pocket (FIGS. 4B and C). The 3$_{10}$-helical conformation is stabilized by two sets of intra-peptide i to i+3 hydrogen bonds: one between the acetyl-capping group at the N-terminus of the peptide and the main- and side chain of the P+1 threonine (FIG. 4C), and the other between the main chain of the P−1 alanine and the main chain of the P+2 glutamate. The P−1 alanine amino group also hydrogen bonds with Asp107 of WDR5 while the main chain of the P+2 glutamate hydrogen bonds with the main chain of the P0 arginine (FIG. 4C). The side chain of the P0 arginine showed extensive hydrogen bonds within the Win motif-binding pocket of WDR5. Furthermore, the position of the P0 arginine guanidinium is sandwiched between two conserved phenylalanines (Phe133 & Phe263) in WDR5, and is likely stabilized by cation-pi interactions. This feature is nearly identical to all previously published Win motif peptide-WDR5 structures. The P+3 valine side chain is solvent exposed and orients the P+4 tyrosine side chain in a region in WDR5 known as the A pocket (FIG. 4E). The A pocket in WDR5 contains residues Tyr191, Pro173, Phe149, and Asp172. As predicted, the P+4 tyrosine hydrogen bonds with the side chain of Asp172 from WDR5 (FIG. 4E). Overall, the structure reveals that all 6 residues in Win6mer play important roles in binding WDR5, which likely explains its improved binding affinity for WDR5 when compared to the previous SET1 family Win motif peptides.

Figure 5:
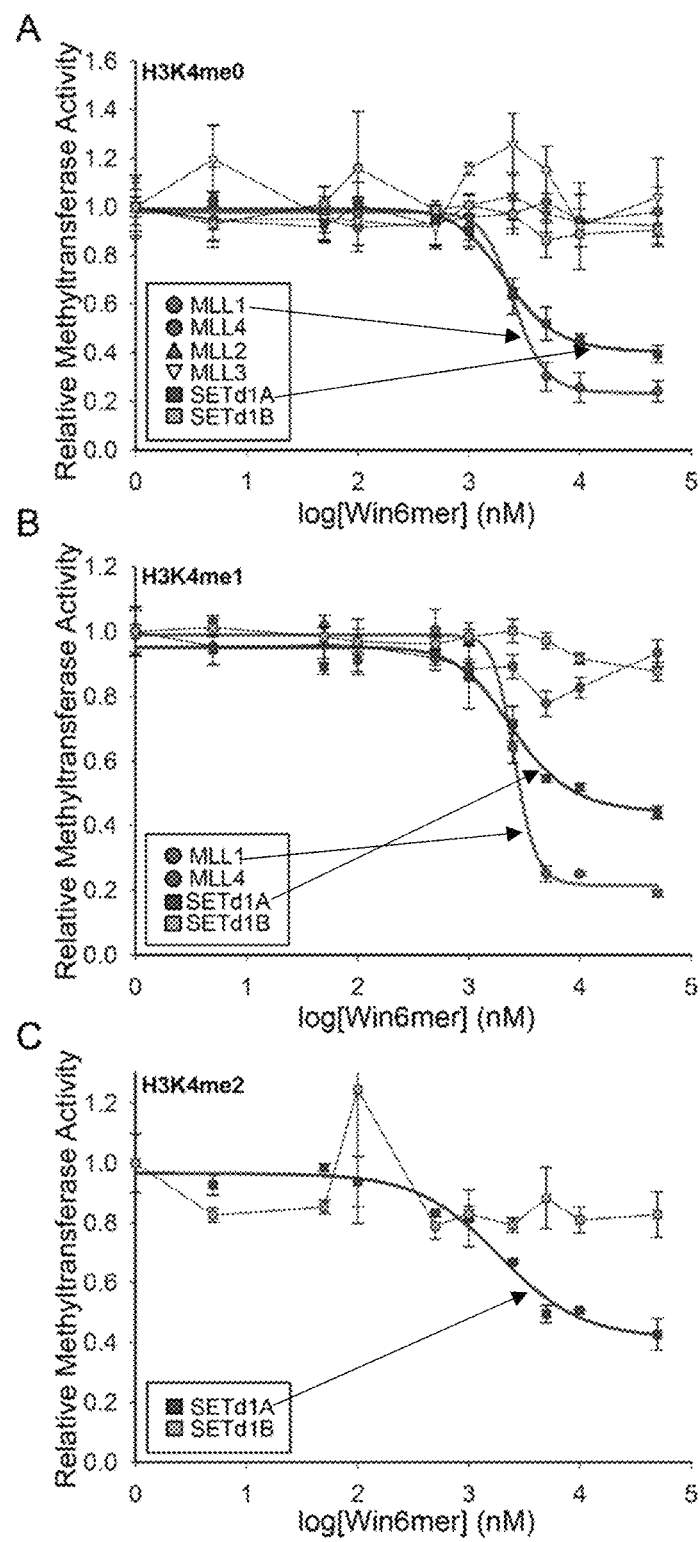
FIG. 5 shows inhibition of SET1 family core complex activity by Win6mer. The activity of SET1 family core complexes upon titration of Win6mer was assessed via scintillation proximity assay. SET1 family core complexes were assayed according to their substrate specificity: (A) All SET1 core complexes were assayed for monomethylation (H3K4me0 substrate). (B) MLL1, MLL4, SETd1A, and SETd1B core complexes were assayed for dimethylation (H3K4me1 substrate). (C) SETd1A and SETd1B core complexes were assayed for trimethylation (H3K4me2 substrate). IC$_{50}$ values are reported on Table III. (D) Efficiency of MLL1 core complex inhibition by Win6mer is dependent on enzyme concentration. IC$_{50}$ values are shown on inset. Activity data for each SET1 family member were normalized to the activity of uninhibited core complex. Data were fit to a dose response with variable slope equation. Monomethyltransferase activity of MLL1-RAD (E) and SETd1A-RAD (F) upon titration of WDR5. Activity data were normalized to the activity of MLL1-RAD or SETd1A-RAD in the absence of WDR5. Data were fit to a dose response with variable slope equation. Error bars represent the S. E. of measurement between 2 independent experiments.
Figure 5:
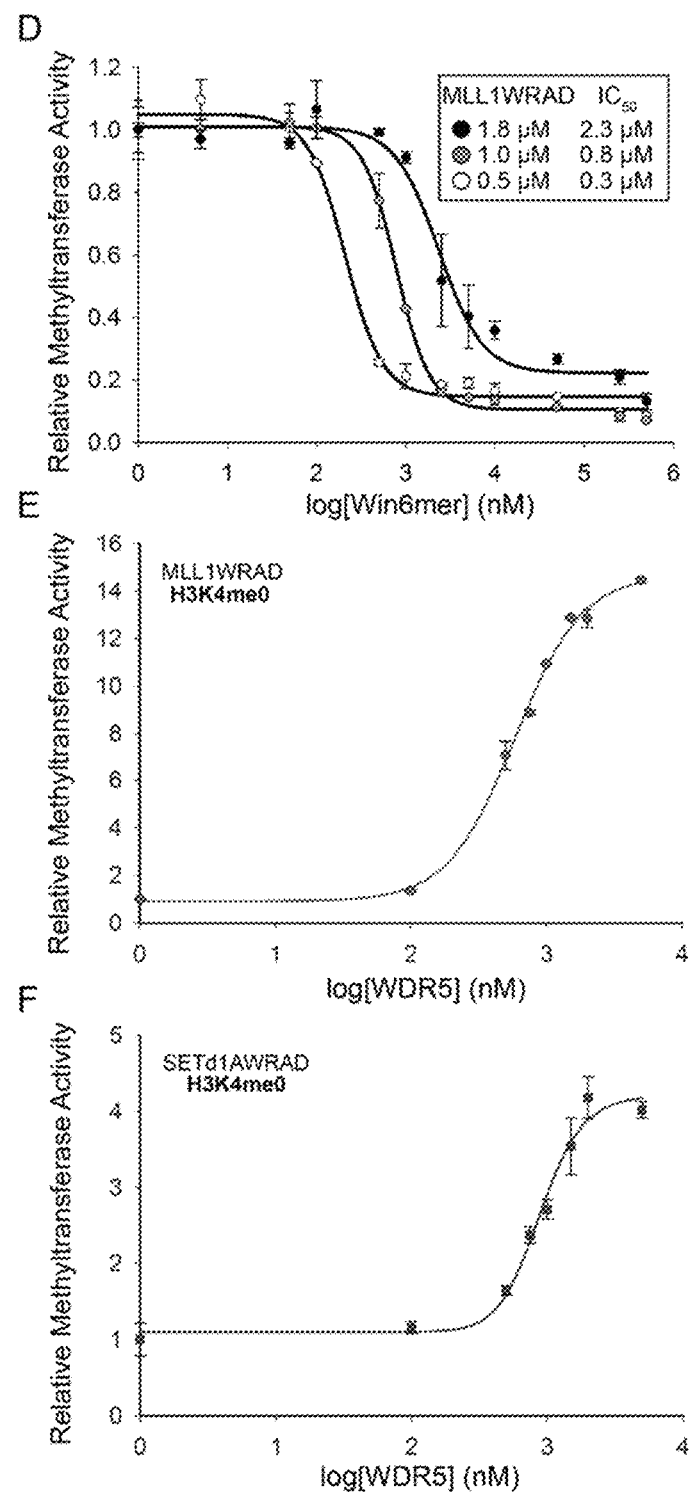

The peptide ARTEVY (SEQ ID NO:8) alters the methyltransferase activities of a subset of SET1 family core complexes. Given that different SET1 family members differ in their requirement for the Win motif-WDR5 interaction for complex assembly and function, we tested whether treatment of the SET1 family of core complexes with the peptide ARTEVY (SEQ ID NO:8) would result in methyltransferase activity patterns that mimic loss of WDR5 or mutation of the Win motif (FIG. 3). To test this, we compared the methyltransferase activity of SET1 core complexes that were treated with increasing concentrations of ARTEVY (SEQ ID NO:8) to that of untreated complexes using radiometric assays. When H3K4me0 was the substrate, we observed that ARTEVY (SEQ ID NO:8) reduced the activity of the MLL1 and SETd1A core complexes in a dose dependent manner (FIG. 5A), while complexes assembled with MLL2-4 and SETd1B were uninhibited. The ARTEVY (SEQ ID NO:8) peptide shows similar inhibition efficiency for MLL1 and SETd1A core complexes, with average IC$_{50}$ values of 2.2 µM and 2.5 µM, respectively (2 µM of enzyme complex assayed) (Table III). Similar inhibition patterns were observed when the H3K4me1 and H3K4me2 peptides were used as substrates (FIGS. 5B and C, respectively). Together, these results show that MLL1 and SETd1A core complexes are specifically inhibited by the Win6mer peptidomimetic that targets the Win motif-WDR5 interaction.

These results raise the question of why MLL1 and SETd1A complexes are specifically targeted over complexes assembled with MLL2-4 and SETd1B. We tested two key variables to account for the differences: 1) affinity of the Win motif for WDR5, and 2) affinity of the RbBP5/ASH2L heterodimer for the SET domain in the absence of WDR5, which influences overall complex stability. We previously found that Win motif peptides derived from the human MLL1 and SETd1A sequences bind WDR5 with significantly weaker affinity ($K_d$=2.8 μM and 0.5 μM, respectively) compared to that of peptides derived from human MLL2-4 and SETd1B sequences ($K_d$ 0.05-0.1 μM) (Table I). These data suggest that the Win motif-WDR5 interaction is more easily disrupted in MLL1 and SETd1A complexes compared to the other complexes. Consistent with the second point, we previously found that complexes assembled with MLL1 and SETd1A rely more heavily on WDR5 for interaction with the RbBP5/ASH2L heterodimer than the other complexes for enzymatic activity. Indeed, we found in this investigation that titration of WDR5 into the MLL1-RAD and SETd1A-RAD complexes showed that stoichiometric amounts of WDR5 are required for full activity (FIGS. 5E and F). Together, these results suggest that WDR5 plays a more crucial role in overall stability of the MLL1 and SETd1A core complexes and are therefore more susceptible to inhibition by molecules that target the WDR5-Win motif interaction. Lastly, our data indicate that the MLL1 and SETd1A complexes have lower overall stabilities compared to other complexes. Consistent with this hypothesis, we observed that the $IC_{50}$ values for the Win6mer were highly dependent on enzyme complex concentration. We found that Win6mer inhibited MLL1 core complex with $IC_{50}$ values of 2.2 μM, 0.8 μM and 0.3 μM when 1.8 μM, 1 μM, and 0.5 μM of enzyme complex were assayed, respectively (FIG. 5D). Lower concentrations of complex shifted the equilibrium towards the unassembled complex, making it easier to gain access to the Win motif-binding pocket on WDR5. Overall, these results suggest that Win6mer preferentially inhibits the methylation activities of MLL1 and SETd1A core complexes due to lower overall complex stability and easier access to the Win motif-binding pocket on WDR5.

The Win6mer peptide disrupts MLL1 and SETd1A core complex assembly, but does not inhibit isolated SET domain activity. Activity assays show that Win6mer selectively downregulates the methyltransferase activity of MLL1 and SETd1A core complexes. This inhibition is most likely due to disruption of the Win motif-WDR5 interaction and destabilization of complex assembly. However, the amino acid sequences of SET1 family Win motifs and Win6mer peptides are somewhat similar to that of the histone H3 N-terminal tail, a SET domain substrate. Thus, it is also possible that the Win6mer may inhibit core complex activity by binding to the SET domain active site. To distinguish between these potential mechanisms of core complex inhibition, we assessed the effects of Win6mer treatment on isolated SET domain activity and on SET1 family core complex assembly.

Figure 6:
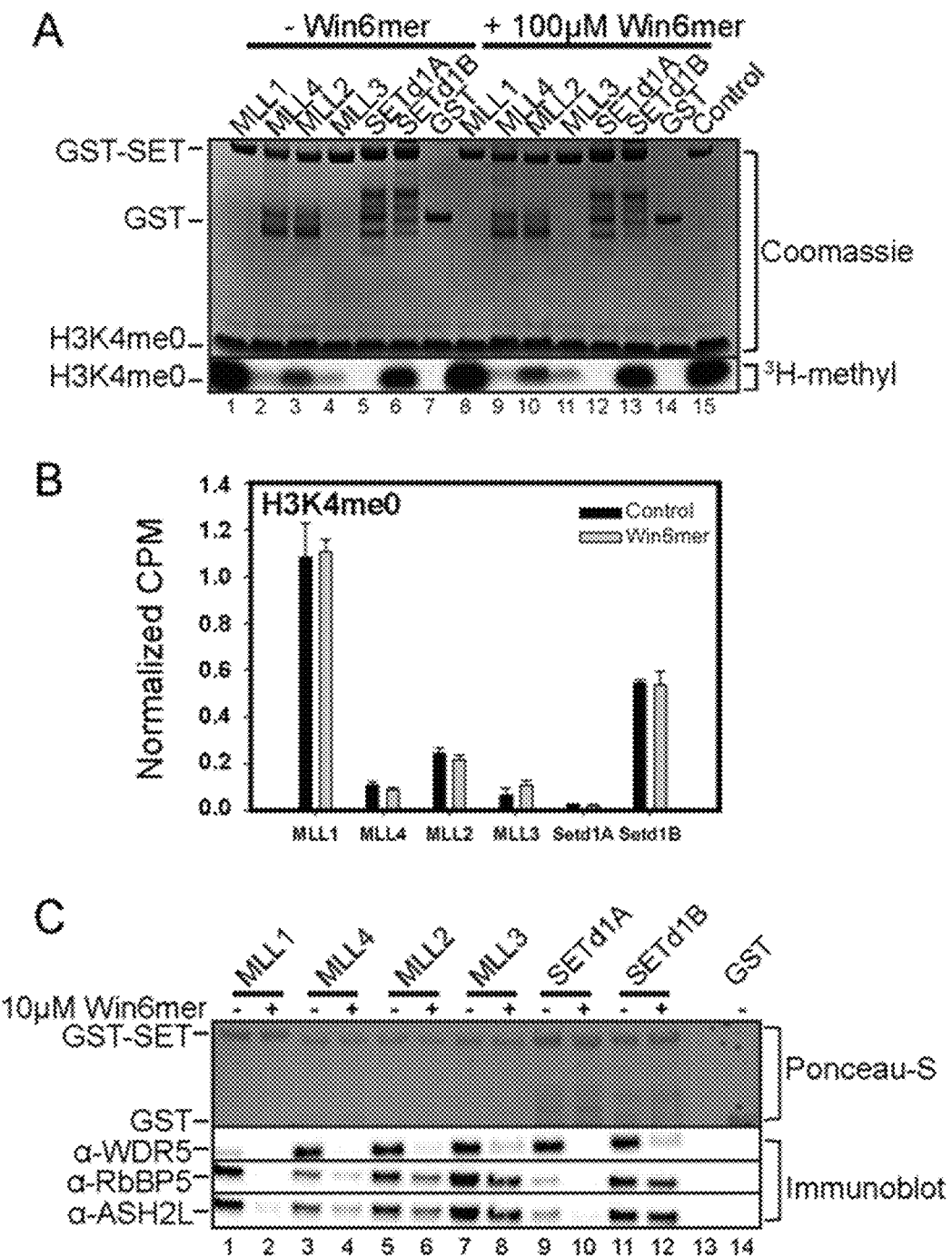
FIG. 6 shows the Win6mer peptide does not target the SET domain directly—essentially showing that it exerts its effects by disrupting complex assembly. (A) Representative gel of a comparison of mono-methyltransferase activities among isolated SET1 family SET domains in the absence of WRAD treated with (100 µM) or without Win6mer. The upper panel shows the Coomassie Blue stained SDS-PAGE gel and the lower panel shows $^3$H-methyl incorporation into H3K4 peptide after 4 h exposure as detected by fluorography. The control lane shows the activity of the MLL1$^{wt}$ SET domain on 100 µM H3K4me0 peptide. (B) Quantification of radioactivity from excised histone H3 peptide bands by LSC. Data are normalized to the activity level of the control lane on each gel. Error bars represent the S. E. of measurement among three independent experiments. (C) Comparison of core complex assembly by SET1 family members from pull-down experiments from MCF-7 cell extracts in the presence (+) (10 µM) or absence (−) of Win6mer. Individual GST-tagged SET domains were incubated with cell extracts and pulled down with glutathione-agarose beads. WRA components were detected by Western blotting. The upper panel shows a Ponceau S-stained PVDF membrane and the lower panels show the immunoblots. GST (not treated with Win6mer) was used as a negative control (lane 14).

First, we tested whether Win6mer inhibits the isolated SET1 family catalytic domains. For this purpose, we treated isolated SET domains with 100 μM Win6mer and assessed their enzymatic activity towards H3 via a radiometric assay. We found that Win6mer treatment did not affect the intrinsic monomethyltransferase activity of SET1 family members (FIGS. 6A and 6B). This suggests that Win6mer does not bind to the SET domain and does not interfere with SET domain-catalyzed H3K4 methylation.

Next, we tested whether Win6mer inhibits core complex activity via disruption or destabilization of core complex assembly. We compared the ability of SET1 family members to interact with endogenous WRAD components from MCF-7 cell extracts in the presence and absence of Win6mer by GST pull-down experiments. Treatment with Win6mer greatly reduced the ability of all six SET1 family members to interact with endogenous WDR5 compared to untreated samples (FIG. 6C). However, we found that Win6mer treatment resulted in a near total loss of RbBP5/ASH2L interaction only with MLL1 and SETd1A complexes (FIG. 6C, compare lanes 1 and 2, and 9 and 10). Other SET1 family members (MLL2, MLL3, MLL4, and SETd1B) showed only a modest reduction in RbBP5/ASH2L binding upon Win6mer treatment when compared to the untreated set (FIG. 6C lanes 3-8, 11 and 12). These results are largely consistent with those observed upon mutation of each SET1 family Win motif (FIG. 2C) and confirm that MLL1 and SETd1A core complexes are more sensitive to complex destabilization by inhibition of the WDR5-Win motif interaction. These results also reveal that the mechanism of inhibition by Win6mer is due to MLL1 and SETd1A core complex destabilization and not competition with histone H3 for binding to the SET domain.

Discussion

In this disclosure, we show that all six human SET1 family members require the Win motif for interaction with WDR5. However, we also observed differences in the role of WDR5 in stabilizing complex assembly and enzymatic activity, suggesting that the Win motif-WDR5 interaction may be conserved for additional functions. In particular, mutation of the Win motif severely disrupts assembly and enzymatic activity of MLL1 and SETd1A complexes, but only modestly disrupts assembly of MLL2/4 and SETd1B complexes, without significant changes in their activity. In contrast, disruption of the Win motif-WDR5 interface does not affect MLL3 core complex assembly, but enhances its enzymatic activity, consistent with previous work. These results raise the question of why the Win motif is highly conserved among metazoan SET1 family members. Our results suggest that WDR5 plays, to varying degrees, a role in complex stabilization for most SET1 family members. Alternatively, it is possible that the Win motif-WDR5 interaction has been retained throughout evolution for additional roles, such as for interaction with other proteins or in gene targeting. Indeed, WDR5 interacts with several transcription factors (e.g. OCT4, MYC), with long non-coding RNAs (e.g. HOTTIP) and PIWI interacting RNAs (e.g. GASS), and has been implicated in recruiting the MLL1 core complex to specific genomic loci.

Our observation that MLL1 and SETd1A require WDR5 for enzymatic activity and complex assembly contrasts with previous reports suggesting that only MLL1 requires WDR5 for these purposes. A possible reason for this discrepancy is that in previous studies enzymatic activity was measured with only the H3K4me0 substrate using an assay that does not distinguish among different methylation states. Indeed, we observed little differences in activity among family members with Win motif mutants in assays using the H3K4me0 substrate with a relatively long incubation period (FIG. 3). Assays conducted with shorter incubation periods within the linear range do show that both MLL1 and SETd1A, but not MLL2-4 and SETd1B core complexes, are sensitive to Win6mer inhibition when H3K4me0 is used as a substrate (FIG. 5A). However, rates of H3K4 di- and trimethylation are most affected by disruption of the Win motif-WDR5 interaction in the human MLL1 and SETd1A complexes, respectively, as both show significantly reduced activity upon mutation of the Win motif or Win6mer treatment under both assay conditions (FIG. 3 and FIGS. 5B and C). The results emphasize the importance of examining the impact of SET1 family inhibitors on each H3K4 methylation state.

Despite conservation of the Win motif, WDR5 recognizes SET1 family Win motifs with significantly different affinities, suggesting a therapeutic window in which to selectively target individual family members. In this disclosure, we describe a new Win motif peptidomimetic (Win6mer) that exploits a unique set of hydrogen bonds that significantly increases affinity for WDR5 compared to other inhibitors. Indeed, Win6mer has the highest reported affinity for the Win motif-binding site on WDR5 when comparing dissociation constants among inhibitors obtained by a direct binding ITC assay (Table I).

Figure 7:
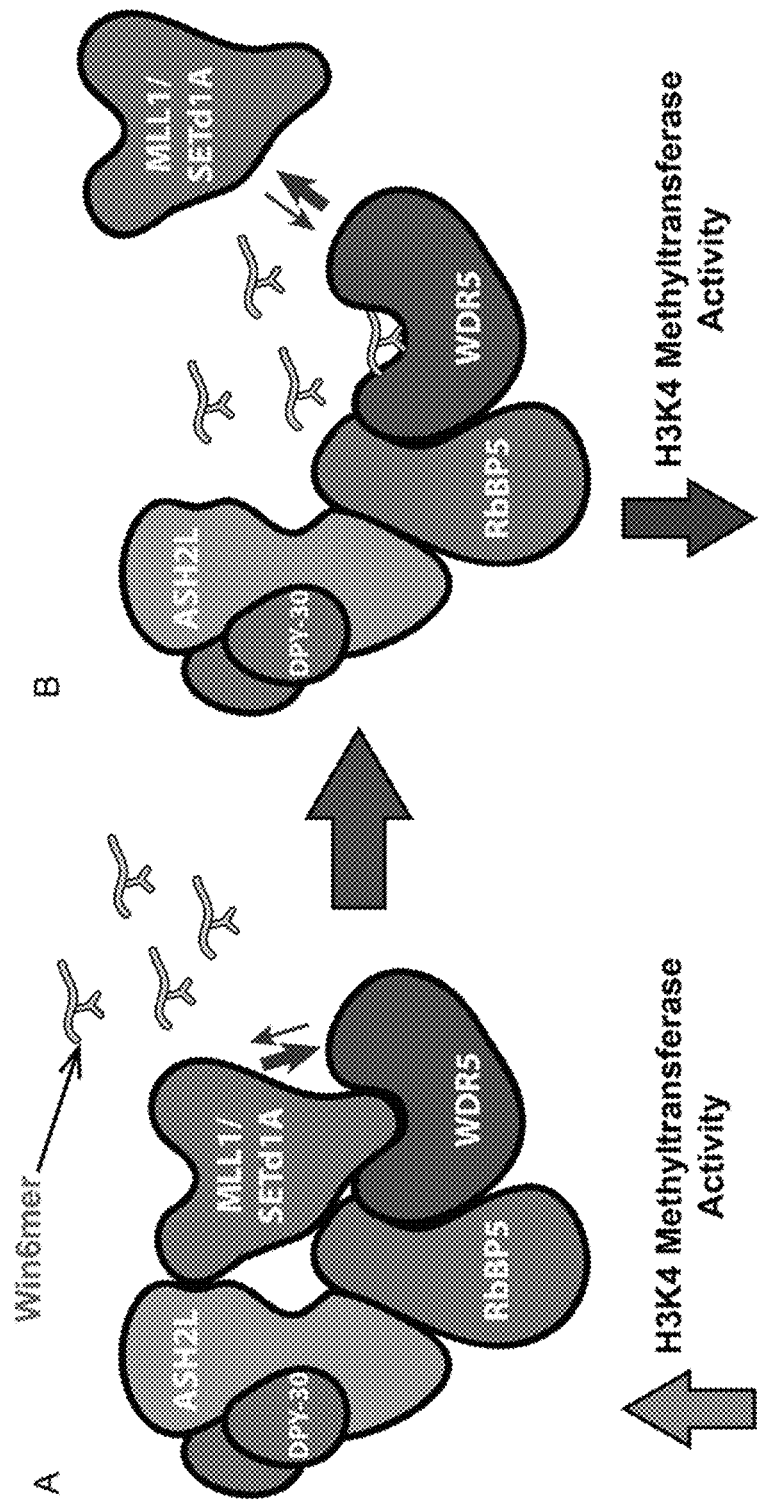
FIG. 7 shows a model for down-regulation of MLL1 and SETd1A core complex activity by Win6mer. (A) MLL1 and SETd1A SET domains require interaction with WDR5 for stabilizing assembly with the components of RAD. Like all SET1 family members, MLL1 and SETd1A utilize the Win motif to interact with WDR5. Stably assembled MLL1 and SETd1A core complexes exhibit full H3K4 methyltransferase activity (B) Treatment with Win6mer, a Win motif peptidomimetic, competes with MLL1 and SETd1A SET domains for WDR5 binding, thus destabilizing core complex assembly. This, in turn, leads to downregulation of MLL1 and SETd1A core complex activity.

We propose that the basis of Win6mer selectivity for MLL1 and SETd1A core complexes lies in the disruption of the Win motif-WDR5 interface, which is required for stabilizing contacts with the RbBP5/ASH2L heterodimer (FIG. 7). MLL1 and SETd1A share the properties that they have the lowest binding affinities for WDR5 and for the RbBP5/ASH2L heterodimer, the combination of which makes them susceptible to inhibition of the Win motif-WDR5 interface. Uncoupling this combination, either through amino acid variation that increases affinity for WDR5 or for the RbBP5/ASH2L heterodimer, renders those complexes less susceptible to inhibition. This explains why the MLL2-4 and SETd1B can retain catalytic activity in the presence of the Win6mer, as they have higher binding affinities for WDR5 or they retain to varying degrees the ability to interact with RbBP5/ASH2L. It is likely that the same mechanism accounts for the inhibition properties of other molecules that target the Win motif-WDR5 interaction.

Experimental Procedures

Materials. WDR5 antibody was obtained from Abcam (ab22512). RbBP5 and ASH2L antibodies were obtained from Bethyl (A300-109A and A300-498A, respectively). An HRP-conjugated donkey anti-rabbit antibody was obtained from GE Healthcare. Anti-Flag M2 agarose beads and anti-Flag (mouse monoclonal M2) antibody were obtained from Sigma. Custom antisera directed against WDR5, CFP1, and WDR82 were prepared as described. HCF1 antiserum was a generous gift from Dr. Winship Herr.

Histone H3 peptides were synthesized by GenScript and contained residues 1-20 followed by GGK-biotin, and were either unmodified (H3K4me0), mono-methylated (H3K4me1), or di-methylated (H3K4me2) at H3K4. All peptides were purified to greater than 95% purity. All H3K4 peptides were modified by amidation of the C-terminus. The 6-mer Win motif peptidomimetic (Win6mer), of sequence Ac-ARTEVY-NH$_2$ (SEQ ID NO:8, where the N-terminus is acetylated and the C-terminus is amidated), was synthesized by GenScript. Win6mer was acetylated on the N-terminus and amidated on the C-terminus to remove charge and improve peptide stability. MCF-7 cell extracts were obtained from Santa Cruz (sc-24793).

Protein expression/purification. Human SET1 family Win-SET cDNAs encoding residues MLL1(3745-3969) (UniProtKB ID Q03164), MLL2(5319-5537) (UniProtKB ID O14686), MLL3(4689-4911) (UniProtKB ID Q8NEZ4), MLL4(2490-2715) (UniProtKB ID Q9UMN6), Setd1A (1474-1708) (UniProtKB ID O15047) and Setd1B(1727-1966) (UniProtKB ID Q9UPS6) were sub-cloned into pGST parallel expression vectors and individually expressed in Escherichia coli (Rosetta II (DE3) pLysS; Novagen) and purified as follows. Briefly, transformed E. coli were grown at 37° C., shaking at 200-220 RPM for approximately 2.5 hours until the OD$_{600}$ reached 0.75. Protein expression was induced with 1 mM IPTG (Isopropyl β-D-1-thiogalactopyranoside) for 26 hours at 16° C., shaking at 200-220 RPM. Cell pellets were resuspended in lysis buffer consisting of Buffer 1 (50 mM Tris (pH 7.5), 300 mM NaCl, 10% glycerol, 3 mM dithiothreitol (DTT), 1 µM ZnCl$_2$), supplemented with cOmplete™ Protease Inhibitor Tablets (Roche Life Sciences) and 0.1 mM PMSF (phenylmethylsulfonyl fluoride). Cells were mechanically lysed using a microfluidizer. Proteins were purified from cleared lysates using a GSTrap-FF column (GE Healthcare) and eluted over a gradient of 0-10 mM reduced glutathione. Pooled fractions were dialyzed with three changes into Buffer 1. Full-length WRAD constructs in pHis parallel expression vectors were individually expressed in E. coli (Rosetta II (DE3) pLysS; Novagen) and purified as previously described. WRAD components were further purified and buffer exchanged by gel filtration chromatography (Superdex 200 HiLoad 16/60, GE Healthcare) pre-equilibrated with 20 mM Tris (pH 7.5), 300 mM NaCl, 1 mM Tris(2-carboxyethyl)phosphine and 1 µM ZnCl$_2$ (Buffer 2). SET1 family mutants were prepared by site-directed mutagenesis (QuikChange II XL, Agilent). DNA sequencing was performed in order to verify that only the intended mutation was introduced. Expression and purification of SET1 family mutants was carried out as described above.

Methyltransferase Assays. MLL core complex Win motif mutants. Histone H3 methyltransferase assays were performed by incubating GST-tagged SET domains (wild type or Win motif mutants) with a stoichiometric amount of WRAD (3 µM final), 1 µCi of $^3$H-AdoMet (Perkin Elmer Inc.), and 100 µM of histone H3 peptides that were unmodified or previously mono- or di-methylated at H3K4 in Assay Buffer (50 mM Tris pH 8.5, 200 mM NaCl, 5 mM MgCl$_2$, 5% glycerol) at 15° C. for 6 hours. 15° C. was chosen as the incubation temperature due to SET domain instability at higher temperatures (unpublished observation). Reactions were quenched with SDS-loading buffer and separated by SDS-PAGE using a 4-12% Bis-Tris gel (Life Technologies) run at 200V for 30 minutes. The gels were enhanced at room temperature for 30 minutes (Enlightning, Perkin Elmer Inc.) then dried for 2.5 hours at 72° C. under constant vacuum. The dried gels were exposed to film (Kodak Biomax MS Film) at −80° C. for 4-24 hours prior to developing. Liquid scintillation counting (LSC) was performed by excising gel bands corresponding to histone H3 peptides, which were dissolved in 750 µL of Solvable (Perkin Elmer Inc.), incubated at room temperature for 30 minutes followed by incubation at 50° C. for 3 hours. The solubilized volume of each sample was transferred to liquid scintillation vials containing 10 mL of Ultima Gold XL liquid scintillation cocktail (Perkin Elmer Inc.). Samples were dark adapted for 1 hour then counted for 5 minutes each with a two-sigma error cut-off using an all-purpose scintillation counter (Beckman Coulter).

MLL Core Complex inhibition by Win6mer. Assay conditions: MLL core complexes were reconstituted by mixing purified GST-SET domains (MLL1, MLL4, MLL2, MLL3, SETd1A, and SETd1B) with WDR5, RbBP5, ASH2L, and DPY-30 in stoichiometric amounts (GST-SET:W:R:A:D 1:1:1:1:2). The activity of each core complex was assessed under the following conditions: 2 µM SET1 core complex, 80 µM biotinylated H3 substrate peptide, 0.68 µM $^3$H-AdoMet (0.5 µCi) at 15° C. in Assay Buffer (50 mM Tris pH 8.5, 200 mM NaCl, 5 mM MgCl$_2$, 5% glycerol), in a total volume of 10 µL. Core complex- or H3 peptide-only reactions incubated with $^3$H-AdoMet served as background controls. Reactions were quenched with 167 mM EDTA (ethylenediaminetetraacetic acid). Each sample was diluted in 50 µL Buffer 2 containing 0.2 mg/mL BSA and then transferred to 96-well streptavidin-coated FlashPlate® Microplates (Perkin Elmer). Samples were incubated overnight at 4° C. to allow binding of the biotinylated H3 peptide to the streptavidin-coated surface prior to scintillation counting in Hidex Sense microplate reader (LabLogic). Determination of linear ranges: The activity of MLL core complexes towards H3K4me0, H3K4me1, or H3K4me2 substrate peptides was assayed as described above. Reactions were quenched at varying time points with 167 mM EDTA and prepared for scintillation counting on Streptavidin FlashPlates®. A plot of counts per minute (CPM) vs. time was constructed from which the linear range was determined. Single time points within the linear range were selected for each SET1 core complex for performing inhibition studies: H3K4me0: MLL1, MLL2*, SETd1A, and SETd1B*—5 min, MLL4—3 min, MLL3—15 min. H3K4me1: MLL1—5 min, MLL4—3 min, SETd1A—15 min, SETd1B—45 min. H3K4me2: SETd1A—2 hr, SETd1B—1 hr. (*1 µM of MLL2 and SETd1B core complex were used for H3K4me0 reactions). Dose response curves: Inhibition studies were performed in order to determine the efficiency of Win6mer as an MLL core complex inhibitor. The activity of each MLL core complex towards H3 substrate peptides was assessed (as described above) with increasing doses of Win6mer (0, 0.005, 0.05, 0.10, 0.5, 1.0, 2.5, 5.0, 10.0, and 50 µM). Reactions were quenched with 167 mM EDTA at the determined time points and prepared for scintillation counting on streptavidin-coated FlashPlastes® as described above.

The activity of SET1 core complexes at each Win6mer concentration point was normalized to the activity of the uninhibited core complex to obtain the relative methyltransferase activity. Inhibition data were plotted as relative methyltransferase activity vs. log [Win6mer] (nM). The Win6mer $IC_{50}$ values for MLL1 and SETd1A core complexes were determined by fitting the data to a dose response with variable slope equation in Sigma Plot.

WDR5 titration into MLL1- and SETd1A-RAD. GST-MLL1 and GST-SETd1A were mixed with RbBP5, ASH2L, and DPY-30 in stoichiometric amounts (SET:R:A:D 1:1:1:2). WDR5 was then titrated into the GST-SET-RAD mixtures at the following final concentrations: 0.1, 0.5, 0.75, 1.0, 1.5, 2.0, 5.0 µM. Methyltransferase activity towards H3K4me0 substrate was assessed as described in "Assay conditions."

The activity of MLL1- and SETd1A-RAD at each WDR5 concentration point was normalized to the activity of the MLL1- and SETd1A-RAD without WDR5 to obtain the relative methyltransferase activity. Data points were plotted as relative methyltransferase activity vs. log [WDR5] (nM).

MLL SET domains treated with Win6mer. Isolated SET1 family SET domains (5 µM) were incubated with 1 µCi of $^3$H-AdoMet (Perkin Elmer Inc.) and 100 µM of H3K4me0, H3K4me1, or H3K4me2 peptides, with and without 100 µM Win6mer, in Assay Buffer at 15° C. for 8 hours. Reactions were quenched with SDS-loading buffer. Fluorography and LSC was carried out as described above.

GST Pull-downs and immunoblots. GST tagged SET1 family proteins were pre-incubated with a stoichiometric amount of purified WDR5 (3 µM) for 1 hour at 4° C. before being added to pre-washed agarose beads coated with glutathione (Thermo Fisher) and incubated for an additional 2 hours at 4° C. with rotation. The beads were washed 3 times with Buffer 2 supplemented with 0.05% Triton X-100 and 0.05% sodium deoxycholate. The complexes were eluted from beads by boiling the samples at 95° C. in SDS-loading buffer for 10 minutes. Samples of the supernatant were run on a 4-12% Bis-Tris gel (Life Technologies) and either stained with Coomassie Brilliant Blue or transferred to a PVDF membrane (Life Technologies) for 1 hour at 30V.

For pull-down assays using cell extracts, a 3 µM concentration of each GST-tagged SET domain was incubated with 100 µg of MCF-7 cell extract for 16 hours at 4° C. Following the initial incubation, 20 µL of a 50:50 slurry of glutathione agarose beads was added to each sample and incubated for an additional 2 hours at 4° C. Samples were washed 3× in radioimmunoprecipitation (RIPA) buffer. Samples were eluted from beads by boiling the samples at 95° C. in SDS-loading buffer for 10 minutes. Samples of the supernatant were separated on a 4-12% Bis-Tris gel and transferred to a PVDF membrane at 30V for 1 hour. PVDF membranes were blocked for 1 hour with a 5% non-fat milk solution then incubated with primary antibody (1:2,000) for 1 hour at room temperature. Blots were washed 4 times then incubated with an HRP-conjugated anti-rabbit secondary antibody (1:5,000) for 1 hour at room temperature. Blots were washed an additional 4 times, then visualized by chemiluminesence (Clarity Western, BioRad) on a BioRad ChemiDoc MP Imager using the chemiluminesence setting.

Co-immunoprecipitation from mammalian cells. Inducible human embryonic kidney (T-REx HEK293) cells were transfected with pcDNA5/TO-Flag-tagged SETd1A or pcDNA5/TO-Flag-tagged SETd1B constructs expressing either the wild type or Win motif mutants, and stably transfected cells selected with hygromycin B, as described previously. Following induction with doxycycline, nuclear extracts were prepared as described and incubated with anti-Flag M2 agarose beads (Sigma) for 3 h. Bound proteins were eluted with SDS sample buffer after extensive washing and analyzed by Western blotting.

Isothermal titration calorimetry (ITC). Purified full-length WDR5 and Win6mer peptide were extensively dialyzed in separate Micro Float-A-Lyzer® Dialysis Devices, MWCO 500-1000 Da (Spectrum Labs) against sample buffer consisting of 20 mM Tris pH 7.5, 300 mM NaCl, 1 mM TCEP, 1 µM $ZnCl_2$ buffer. ITC experiments were carried out at 20° C. using a VP-ITC micro-calorimeter (MicroCal). After an initial delay of 120 sec, Win6mer (200 µM) was titrated into the experimental cell containing full-length WDR5 (20 µM) over the course of 45 injections, 5 µL each. Reference power was set to 10 µCal/sec and stirring speed was set to 295 rpm. Data were integrated using NITPIC. SEDPHAT was used to fit the integrated data to a single-site heterogeneous association model, using simulated annealing and Maxquardt-Levenberg algorithms. Automatic confidence interval search with projection method was applied to estimate the error of the determined thermodynamic parameters. Confidence interval was set to 2σ (95%). ITC figure was generated using GUSSI.

Crystallization and structure determination. A WDR5ΔN construct (23-334) was purified as previously described. The final prep buffer contained 20 mM Tris (pH 7.5), 150 mM NaCl, 1 mM Tris(2-carboxyethyl)phosphine and 1 µM $ZnCl_2$. Crystals of the WDR5ΔN-Win6mer binary complex were obtained by hanging drop vapor diffusion. Prior to crystallization, a 45 mg/mL stock solution of WDR5ΔN was mixed with a 10 mM stock solution of Win6mer dissolved in water. The final concentrations of WDR5ΔN and Win6mer were 350 µM and 700 µM, respectively. Initial crystals were obtained from screening with the JCSG Core I Suite in a condition consisting of 0.1M sodium citrate pH 5.6, 20% (v/v) isopropanol, and 20% (w/v) polyethylene glycol (PEG) 4000. Crystals were reproduced by manual screening of initial conditions and were observed in a condition containing 0.1M sodium citrate pH 5.6, 15% (v/v) isopropanol, and 17% (w/v) PEG 4000. Hampton Research Additive Screen was used for further optimization. The final crystallization condition contained 0.1M sodium citrate pH 5.6, 15% 2-propanol, and 17% PEG 4000, and 10 mM ATP. The crystals were flash frozen in the final mother liquor containing 25% ethylene glycol as a cryoprotectant.

X-ray diffraction data were collected on the F1 beam-line at the Cornell High Energy Synchrotron Source (Ithaca, N.Y.) using an ADSC Quantum 270 CCD detector. The data set was indexed, reduced, and scaled with HKL-2000. Data were originally scaled to a resolution limit of 1.9 Å and then resealed to 2.0 Å as the resolution limit cut-off was set to 2.0 Å during refinement. Data collection statistics of the resealed data set are reported in Table II. Initial phases were obtained by molecular replacement with Phaser using the coordinates from the WDR5 apo-structure (PDB ID 2H14) as the search model. After an initial rigid body refinement, auto-building was performed using ARP/WARP. Standard structural modeling and refinement were performed with Coot and PHENIX, respectively. Refinement statistics are summarized in Table II. Validation of the model quality was assessed with MolProbity. All images were made using CCP4 mg. Crystallographic software was accessed through SBGrid. The coordinates for the WDR5-Win6mer structure have been deposited to the Protein Data Bank, PDB ID: 5SXM.

TABLE II

X-ray data collection and refinement statistics.

| Data collection | |
|---|---|
| Space group | P 3$_1$ |
| Cell | |
| a, b, c (Å) | 74.9, 74.9, 93.5 |
| α, β, γ (°) | 90.0, 90.0, 120.0 |
| X-Ray Source | MacCHESS F1 |
| Wavelength (Å) | 0.977 |
| Resolution (Å) | 50.0-2.00 (2.07-2.00) |
| Total reflections | 330393 |
| Unique reflections | 39482 |
| Completeness (%) | 100.0 (100.0) |
| Rsym(%) | 11.7 (56.8) |
| <I/σ(I)> | 32.2 (5.0) |
| Multiplicity | 8.4 (7.9) |
| Wilson B factor (Å$^2$) | 26.1 |

TABLE II-continued

X-ray data collection and refinement statistics.

| Refinement | |
|---|---|
| Resolution (Å) | 37.95-2.00 (2.05-2.00) |
| R factor (%) | 21.4 (30.4) |
| Free R factor (%) | 24.3 (36.3) |
| Free R reflections (%) | 4.9 |
| No of free R reflections | 1955 |
| Molecules in AU | 2 |
| Residue Range Built | A/31-334, B/32-334, C/1-6, D/1-6 |
| No. of non-H atoms | 5143 |
| No. of water molecules | 272 |
| Model quality | |
| R.m.s.d. bond lengths (Å) | 0.003 |
| R.m.s.d. bond angles (°) | 0.884 |
| Mean B factors (Å$^2$) | |
| Overall | 31.3 |
| Chain A | 32.9 |
| Chain B | 32.8 |
| Chain C (Win6mer) | 26.6 |
| Chain D (Win6mer) | 26.5 |
| Water | 37.5 |
| Ramachandran plot (%) | |
| Favored | 96.5 |
| Allowed | 3.2 |
| Disallowed | 0.3 |

TABLE III

Win6mer inhibition efficiency of SET1 family core complexes.

| Core Complex | Inhibition Efficiency, IC$_{50}$ (μM) [95% confidence interval] | | |
|---|---|---|---|
| | H3K4me0 | H3K4me1 | H3K4me2 |
| MLL1 | 2.3 [1.6-3.3] | 2.2 [1.7-2.8] | n/a |
| MLL4 | — | — | n/a |
| MLL2 | — | n/a | n/a |
| MLL3 | — | n/a | n/a |
| SETd1A | 3.2 [2.0-5.2] | 2.9 [1.7-5.1] | 2.4 [1.4-4.1] |
| SETd1B | — | — | — | n/a = not applicable due to substrate specificity
— = not inhibited at tested Win6mer concentrations Although the present disclosure has been described with respect to one or more particular embodiments and/or examples, it will be understood that other embodiments and/or examples of the present disclosure may be made without departing from the scope of the present disclosure.

The invention claimed is:

1. A peptide that inhibits the formation of or disrupts MLL1 and SET1 complexes, wherein the peptide is 6-50 amino acid long and comprises the following sequence: $ARX_1X_2X_3X_4$ (SEQ ID NO:1), wherein $X_1$ is A, S, L, V, W, Y, or T; $X_2$ is E or Q; $X_3$ is V, P, or G; and $X_4$ is Y, K, or R, and wherein the N-terminus of the peptide is acetylated or the C-terminus is amidated.

2. The peptide of claim 1, wherein $ARX_1X_2X_3X_4$ (SEQ ID NO:1) has the following sequence: ARTEVY (SEQ ID NO:8) or ARTEPY (SEQ ID NO:9).

3. The peptide of claim 1, wherein the peptide is 6 amino acid long.

4. The peptide of claim 1, wherein the N-terminus of the peptide is acetylated and the C-terminus is amidated.

5. The peptide of claim 3, wherein the N-terminus of the peptide is acetylated and the C-terminus is amidated.

6. The peptide of claim 1, wherein the peptide is intramolecularly stapled.

7. A composition comprising a peptide of claim 1 and a pharmaceutically acceptable carrier.

8. The composition of claim 7, wherein the peptide is 6 amino acids long.

9. The composition of claim 7, wherein $ARX_1X_2X_3X_4$ (SEQ ID NO: 1) is ARTEVY (SEQ ID NO:8) or ARTEPY (SEQ ID NO:9).

10. A method of inhibiting the growth of cancer cells comprising administering to an individual in need of treatment a composition of claim 7 wherein the administration results in reducing the growth of cancer cells.

11. The method of claim 10, wherein the peptide of the composition is 6 amino acids long.

12. The method of claim 10, wherein ARX$_1$X$_2$X$_3$X$_4$ (SEQ ID NO: 1) is ARTEVY (SEQ ID NO:8) or ARTEPY (SEQ ID NO:9).

13. The method of claim 10, wherein cancer is infant acute lymphocyctic leukemia, de novo acute myeloid leukemia, or a solid tumor.

14. The method of claim 10, wherein the administration is combined with chemotherapy, radiation therapy, surgical removal of tumors, or combinations thereof.

15. The composition of claim 7, wherein the N-terminus of the peptide is acetylated and the C-terminus is amidated.

16. The method of claim 10, wherein the N-terminus of the peptide is acetylated and the C-terminus is amidated.

* * * * *

UNITED STATES PATENT AND TRADEMARK OFFICE
CERTIFICATE OF CORRECTION

PATENT NO. : 10,392,423 B2
APPLICATION NO. : 15/939604
DATED : August 27, 2019
INVENTOR(S) : Cosgrove et al.

Page 1 of 1

It is certified that error appears in the above-identified patent and that said Letters Patent is hereby corrected as shown below:

In the Claims

In Claim 13:
Column 27, Line 11, "lymphocyctic" should read: --lymphocytic--.

Signed and Sealed this
Eighteenth Day of February, 2020

Andrei Iancu
*Director of the United States Patent and Trademark Office*

SEQUENCE LISTING

<160> NUMBER OF SEQ ID NOS: 10

<210> SEQ ID NO 1
<211> LENGTH: 6
<212> TYPE: PRT
<213> ORGANISM: Artificial Sequence

```
<220> FEATURE:
<223> OTHER INFORMATION: Synthetic peptide
<220> FEATURE:
<221> NAME/KEY: VARIANT
<222> LOCATION: (3)..(3)
<223> OTHER INFORMATION: X  = A, S, L, V, W, Y, or T
<220> FEATURE:
<221> NAME/KEY: VARIANT
<222> LOCATION: (4)..(4)
<223> OTHER INFORMATION: X  = E or Q
<220> FEATURE:
<221> NAME/KEY: VARIANT
<222> LOCATION: (5)..(5)
<223> OTHER INFORMATION: X  = V, P, or G
<220> FEATURE:
<221> NAME/KEY: VARIANT
<222> LOCATION: (6)..(6)
<223> OTHER INFORMATION: X  = Y, K, or R

<400> SEQUENCE: 1

Ala Arg Xaa Xaa Xaa Xaa
1               5

<210> SEQ ID NO 2
<211> LENGTH: 14
<212> TYPE: PRT
<213> ORGANISM: Artificial Sequence
<220> FEATURE:
<223> OTHER INFORMATION: Synthetic peptide

<400> SEQUENCE: 2

Leu Asn Pro His Gly Ser Ala Arg Ala Glu Val His Leu Arg
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic peptide

<400> SEQUENCE: 3

Leu Asn Pro His Gly Ala Ala Arg Ala Glu Val Tyr Leu Arg
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic peptide

<400> SEQUENCE: 4

Ile Asn Pro Thr Gly Cys Ala Arg Ser Glu Pro Lys Ile Leu
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic peptide

<400> SEQUENCE: 5

Val Asn Pro Thr Gly Cys Ala Arg Ser Glu Pro Lys Met Ser
1               5                   10

<210> SEQ ID NO 6
<211> LENGTH: 14
```

```
<212> TYPE: PRT
<213> ORGANISM: Artificial Sequence
<220> FEATURE:
<223> OTHER INFORMATION: Synthetic peptide

<400> SEQUENCE: 6

Glu His Gln Thr Gly Ser Ala Arg Ser Glu Gly Tyr Tyr Pro
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthetic peptide

<400> SEQUENCE: 7

Glu His Gln Thr Gly Ser Ala Arg Ser Glu Gly Tyr Tyr Gly
1               5                   10

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide

<400> SEQUENCE: 8

Ala Arg Thr Glu Val Tyr
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic peptide

<400> SEQUENCE: 9

Ala Arg Thr Glu Pro Tyr
1               5

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide derived from TAT

<400> SEQUENCE: 10

Tyr Gly Arg Lys Lys Arg Arg Gln Arg Arg Arg
1               5                   10
```